(12) United States Patent
Boveja et al.

(10) Patent No.: US 7,191,012 B2
(45) Date of Patent: Mar. 13, 2007

(54) METHOD AND SYSTEM FOR PROVIDING PULSED ELECTRICAL STIMULATION TO A CRANIEL NERVE OF A PATIENT TO PROVIDE THERAPY FOR NEUROLOGICAL AND NEUROPSYCHIATRIC DISORDERS

(76) Inventors: Birinder R. Boveja, P.O. Box 210095, Milwaukee, WI (US) 53221; Angely Widhany, P.O. Box 210095, Milwaukee, WI (US) 53221

(*) Notice: Subject to any disclaimer, the term of this patent is extended or adjusted under 35 U.S.C. 154(b) by 575 days.

(21) Appl. No.: 10/436,017

(22) Filed: May 11, 2003

(65) Prior Publication Data

US 2005/0143786 A1   Jun. 30, 2005

(51) Int. Cl.
*A61N 1/08* (2006.01)
(52) U.S. Cl. .......................................... 607/60; 607/61
(58) Field of Classification Search ................. 607/30, 607/33, 45, 32, 60, 61
See application file for complete search history.

(56) References Cited

U.S. PATENT DOCUMENTS

| | | | | |
|---|---|---|---|---|
| 4,702,254 A | 10/1987 | Zabara et al. | ............... | 128/421 |
| 4,867,164 A | 9/1989 | Zabara et al. | ............... | 128/421 |
| 5,025,807 A | 6/1991 | Zabara et al. | ............... | 128/421 |
| 5,928,272 A | 7/1999 | Adkins et al. | ................ | 607/45 |
| 5,938,584 A | 8/1999 | Ardito et al. | .................. | 607/38 |
| 6,205,359 B1 | 3/2001 | Boveja | ......................... | 607/45 |
| 6,208,902 B1 | 3/2001 | Boveja | ......................... | 607/46 |
| 6,269,270 B1 | 7/2001 | Boveja | ......................... | 607/45 |
| 6,505,074 B2 | 1/2003 | Boveja et al. | ................ | 607/41 |
| 6,662,052 B1 * | 12/2003 | Sarwal et al. | ................. | 607/59 |
| 6,735,474 B1 | 5/2004 | Loeb et al. | .................... | 607/41 |
| 6,760,626 B1 | 7/2004 | Boveja | ......................... | 607/59 |
| 6,920,359 B2 * | 7/2005 | Meadows et al. | ............. | 607/59 |
| 6,941,171 B2 | 9/2005 | Mann et al. | ................... | 607/39 |
| 2001/0002441 A1 | 5/2001 | Boveja | ......................... | 607/46 |
| 2002/0013612 A1 * | 1/2002 | Whitehurst | .................. | 607/45 |
| 2002/0013613 A1 * | 1/2002 | Haller et al. | .................. | 607/60 |
| 2002/0055761 A1 | 5/2002 | Mann et al. | ................... | 607/41 |
| 2002/0087192 A1 | 7/2002 | Barrett et al. | .................. | 607/2 |
| 2002/0183799 A1 * | 12/2002 | Silvian | ........................ | 607/32 |
| 2003/0004553 A1 | 1/2003 | Grill et al. | ..................... | 607/40 |
| 2003/0236558 A1 * | 12/2003 | Whitehurst et al. | ........... | 607/45 |
| 2005/0049655 A1 | 3/2005 | Boveja et al. | ................ | 607/58 |
| 2005/0187590 A1 | 8/2005 | Boveja et al. | ................ | 607/45 |

* cited by examiner

*Primary Examiner*—Mark Bockelman

(57) ABSTRACT

A method and system for providing electrical pulses for neuromodulating a cranial nerve of a patient utilizing an implantable stimulator. The implantable stimulator comprising a pulse generator module and a stimulus receiver module for coupling with an external stimulator. Control circuitry ensures selective operation of one pulse generator module. The external stimulator comprises a telemetry module for remotely activating (or de-activating) programs over the internet, to arrive at the optimal program for each patient. Once the optimal "dose" is titrated using the external stimulator, the implanted pulse generator can then be programmed to such parameters. The external stimulator in conjunction with the implanted stimulus receiver can override the implanted pulse generator, to provide extra dose of therapy or to conserve the implanted battery. The external stimulator is also networked to other computers. The external programmer may also comprise a global positioning system (GPS) module for determining patient location.

30 Claims, 41 Drawing Sheets

| Axons from skin | A α | Aβ | Aδ | C |
|---|---|---|---|---|
| Axons from muscles | Group I | II | III | IV |
| Diameter (μm) | 13-20 | 6-12 | 1-5 | 0.2-1.5 |
| Speed (m/sec) | 80-120 | 35-75 | 5-30 | 0.5-2 |
| Sensory receptors | Proprioceptors of skeletal muscle | Mechanoreceptors of skin | Pain temperature | Temperature, pain, itch |

FIG. 7

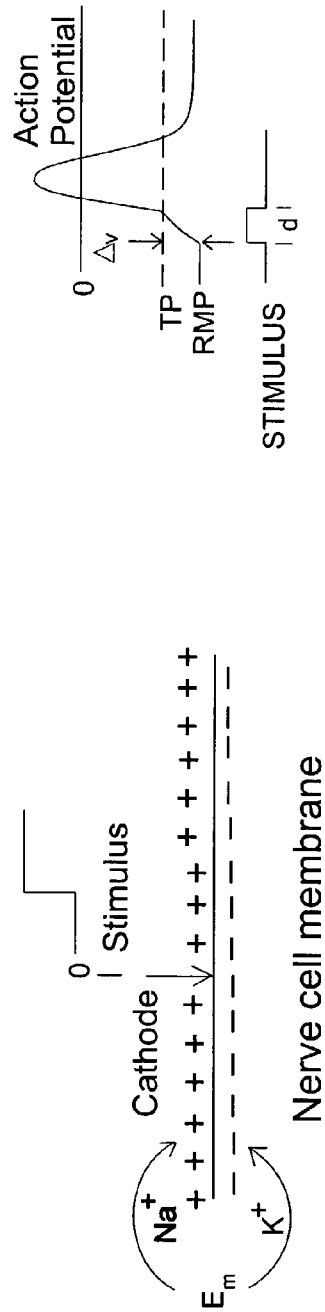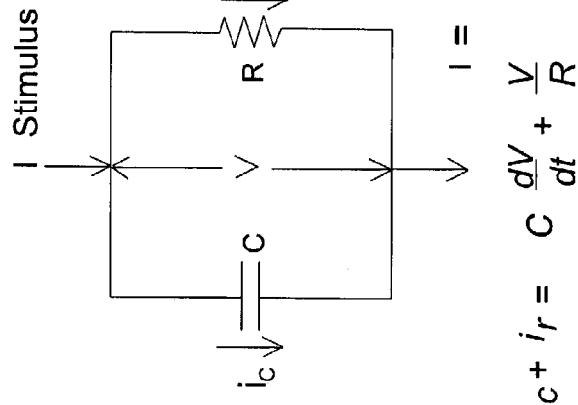
FIG 8B
FIG 8C
FIG 8A

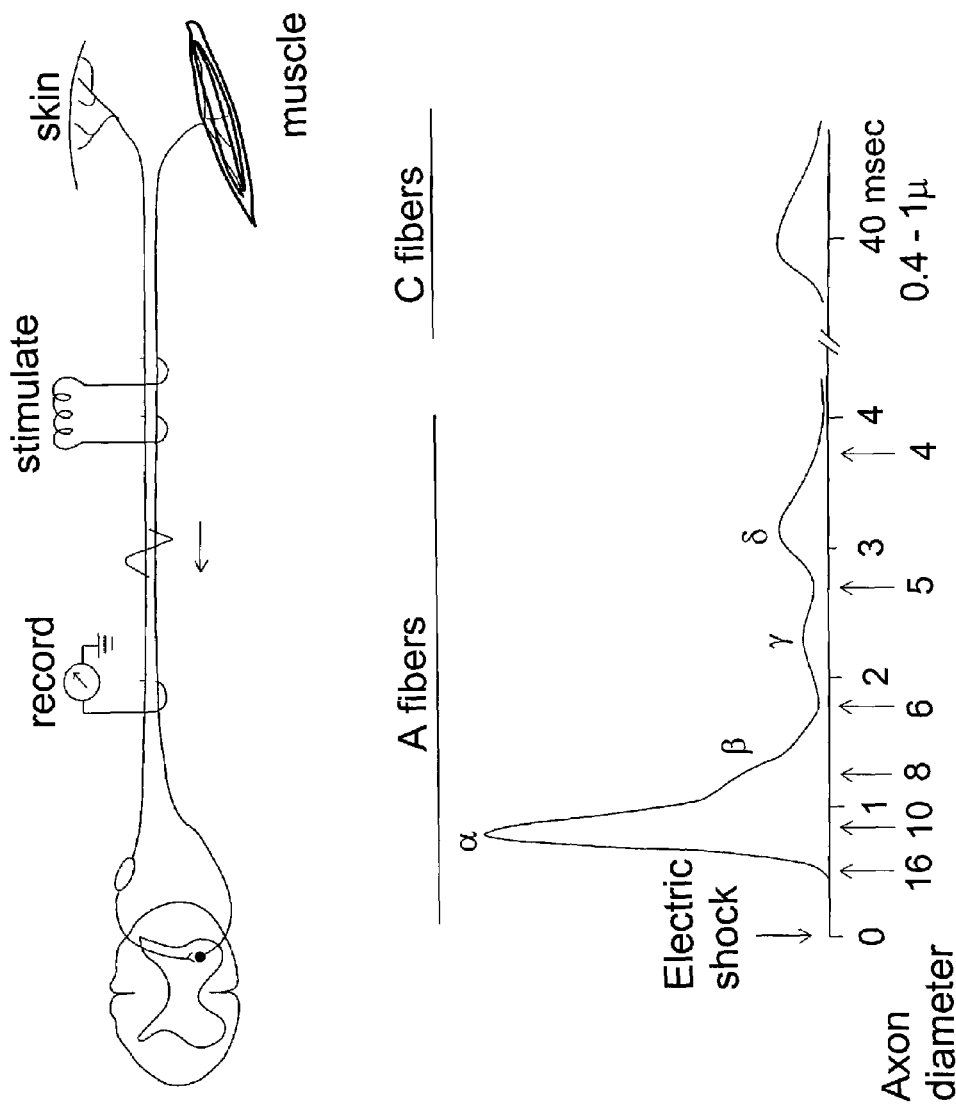

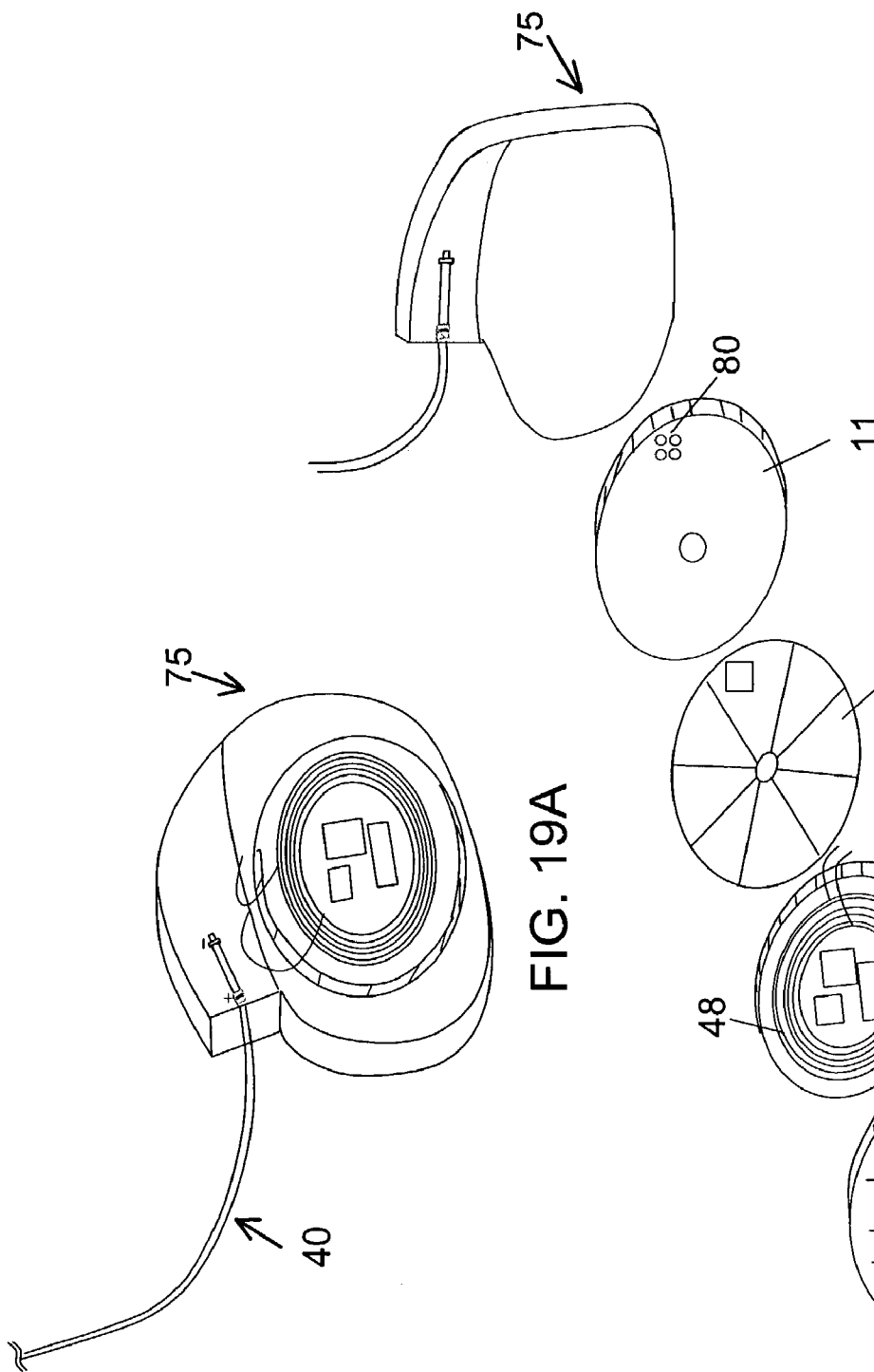

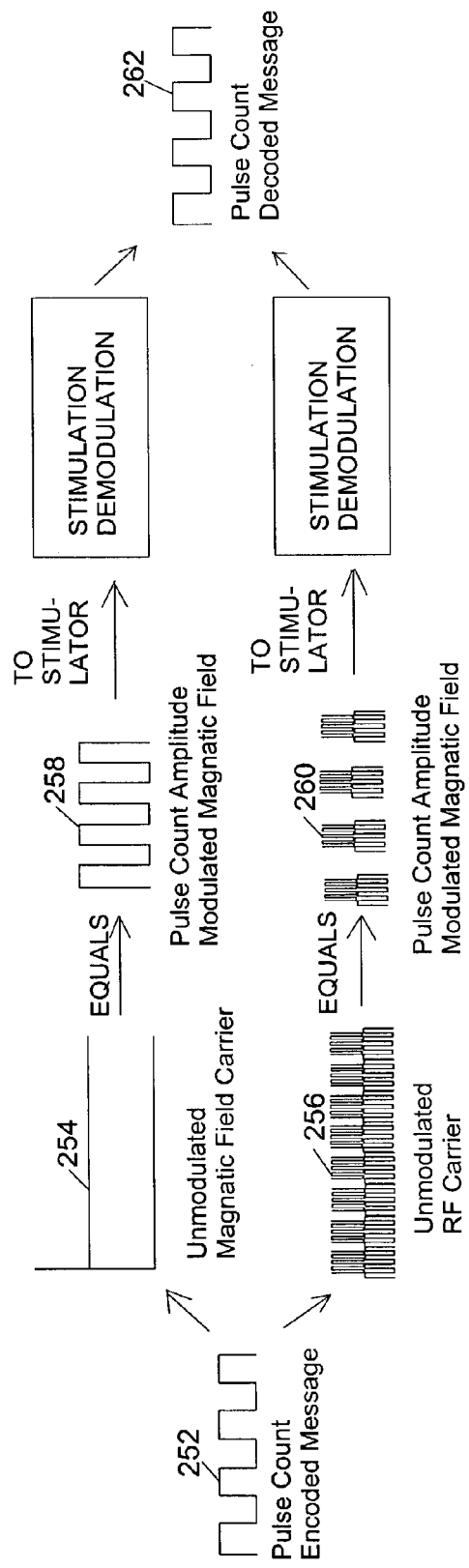
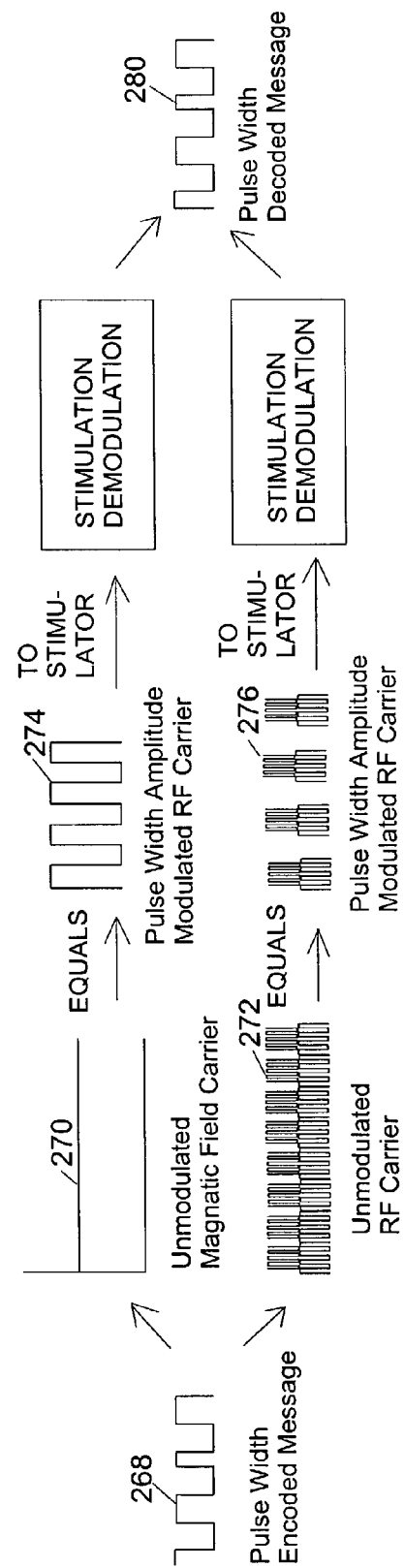
FIG. 23 A
FIG. 23 B

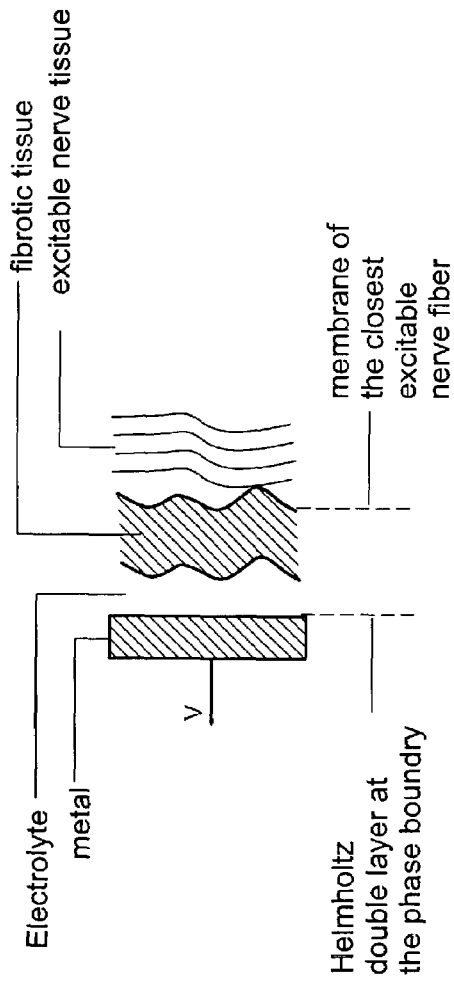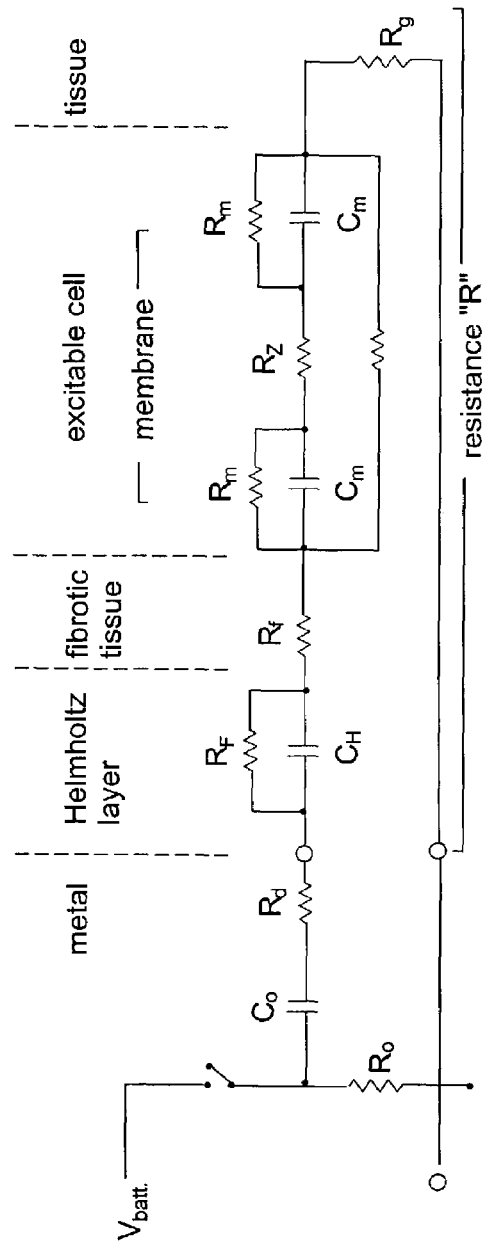
FIG. 32A
FIG. 32B

METHOD AND SYSTEM FOR PROVIDING PULSED ELECTRICAL STIMULATION TO A CRANIEL NERVE OF A PATIENT TO PROVIDE THERAPY FOR NEUROLOGICAL AND NEUROPSYCHIATRIC DISORDERS

FIELD OF INVENTION

The present invention relates to neuromodulation, more specifically a method and system for neuromodulation of a vagus nerve to provide therapy for neurological and neuropsychiatric disorders by providing electrical pulses with an implanted stimulus receiver/pulse generator.

BACKGROUND

The vagus nerve is the 10th cranial nerve in the body. Vagus nerve stimulation, and the profound effects of electrical stimulation of the vagus nerve on central nervous system (CNS) activity, extends back to the 1930's. Medical studies in clinical neurobiology have advanced our understanding of anatomic and physiologic basis of the effects of vagus nerve stimulation.

Afferent neuromodulation of the vagus nerve has clinical efficacy for various neurological and neuropsychiatric disorders, such as partial complex epilepsy, generalized epilepsy, parkinsonson's disease, migraines, severe depression, Alzheimer's disease, anxiety disorders, obsessive compulsive disorders, and the like. Prior art discloses implanted pulse generator (IPG) system, and inductively coupled system using an implanted stimulus receiver and an external stimulus transmitter.

An IPG system for neuromodulation granted to Zabara U.S. Pat. Nos. 4,702,254, 4,867,164, and 5,025,807, discloses essentially "cardiac pacemaker-like" technology applied to stimulating a vagus nerve. Such system and method, though convenient has the disadvantage that internal battery will not last for a desired period of time, which can lead to repeated surgeries for generator replacement. Also, because of the concern for battery longevity, optimal therapy for giving electrical pulses is usually not utilized since that would lead to excessive battery drain. Further, the programming of the stimulation parameters is performed by the medical staff and requires a visit to the physician's office or the clinic when a program change has to be made. Thus, the prior art has a cumbersome process of adjusting the therapy levels.

An inductively coupled system and method for neuromodulation granted to Boveja U.S. Pat. Nos. 6,205,359 B1, 6,269,270 B1, and 6,356,788 B2 overcomes many of the disadvantages of an IPG system such as battery life, and easier activation of programs by the patient, but patient convenience remains an issue since a secondary coil has to be kept in close proximity to an implanted primary coil. It would be desirable to have the advantages of both an IPG system and an inductively coupled system. The system and method disclosed, provides an improved method and system for adjunct therapy by providing a system that has the benefits of both systems, and has additional synergistic benefits not possible in the prior art. In this application the patient can choose when to use an external inductively coupled system to conserve the battery life of the implanted module and receive higher levels of therapy.

The current application discloses an implanted medical device capable of being used as a programmable implanted pulse generator (IPG), or as a stimulus-receiver for an inductively coupled system with power being supplied by an external stimulator, as is shown in FIGS. 1 and 2. The external stimulator also being remotely controllable from a distant location via the internet. Controlling circuitry within the device, makes the inductively coupled stimulator and the IPG operate in harmony with each other, as described later. For example, when stimulation is applied via the inductively coupled system, the battery operated portion of the stimulator is triggered to go into the "sleep" mode. Conversely, when programming pulses (also inductively coupled) are being applied to the battery operated pulse generator, the inductively coupled stimulation circuitry is disconnected.

In the method and system of the current invention, after the system is implanted in the patient, optimal stimulation parameters are "titrated" for the condition of the individual patent. Clinical research has shown that each patient is biologically unique and responds little bit differently to given stimulation. The inductively coupled stimulation part of the system is a very convenient method of adjusting the parameters for stimulation therapy, that would be optimally suited for each individual patient. Further, as shown in FIG. 3, the external stimulator has a telemetry module and can be controlled remotely via the internet. In one embodiment, numerous pre-determined programs are pre-packaged into the memory of the external stimulator 42. A physician situated remotely is able to selectively activate (and de-activate) selected pre-packaged (pre-determined) programs. As shown in FIGS. 4A and 4B, the telemetry module within the external stimulator wirelessly communicates with a base station 2, either via a server (shown in FIG. 4A) or directly (shown in FIG. 4B). Also, as shown in FIG. 5, a physician in a remote location is able to interrogate and selectively program the external stimulator 43 via a server 130.

Once the appropriate stimulation parameters are determined by "trial and error", the battery operated portion of the implanted pulse generator can be programmed to the optimal electrical stimulation parameters via a programmer 85. For ideal therapy the electrical stimulation parameters need to be adjusted at regular intervals taking into account optimal benefits.

Another distinct advantage of the current system is that when the stimulation is performed via the external stimulator 42, the battery of the implanted pulse generator (IPG) 70 is conserved, extending the life of the implanted system.

Background of Neuromodulation

The $10^{th}$ cranial nerve in the body, or the vagus nerve plays a role in mediating afferent information from visceral organs to the brain. The vagus nerve arises directly from the brain, but unlike the other cranial nerves extends well beyond the head. At its farthest extension it reaches the lower parts of the intestines. The vagus nerve provides an easily accessible, peripheral route to modulate central nervous system (CNS) function. In the human body there are two vagal nerves (VN), the right VN and the left VN. Each vagus nerve is encased in the carotid sheath along with the carotid artery and jugular vein. The innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is known that stimulation of the left vagus nerve does not cause substantial slowing of the heart rate or cause any other significant deleterious side effects.

One of the fundamental features of the nervous system is its ability to generate and conduct electrical impulses. Most nerves in the human body are composed of thousands of fibers of different sizes. This is shown schematically in FIG. 6. The different sizes of nerve fibers, which carry signals to and from the brain, are designated by groups A, B, and C. The vagus nerve, for example, may have approximately 100,000 fibers of the three different types, each carrying signals. Each axon or fiber of that nerve conducts only in one direction, in normal circumstances. Vagus nerve is composed of 80% afferent sensory fibers carrying information to the brain from the head, neck, thorax, and abdomen.

In a cross section of peripheral nerve it is seen that the diameter of individual fibers vary substantially, as is shown schematically in FIG. 7. The largest nerve fibers are approximately 20 μm in diameter and are heavily myelinated (i.e., have a myelin sheath, constituting a substance largely composed of fat), whereas the smallest nerve fibers are less than 1 μm in diameter and are unmyelinated.

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially in the form of the action potential, are taken into consideration when defining the groups. The smallest fibers (group C) are unmyelinated and have the slowest conduction rate, whereas the myelinated fibers of group B and group A exhibit rates of conduction that progressively increase with diameter.

Nerve cells have membranes that are composed of lipids and proteins, and have unique properties of excitability such that an adequate disturbance of the cell's resting potential can trigger a sudden change in the membrane conductance. Under resting conditions, the inside of the nerve cell is approximately −90 mV relative to the outside. The electrical signaling capabilities of neurons are based on ionic concentration gradients between the intracellular and extracellular compartments. The cell membrane is a complex of a bilayer of lipid molecules with an assortment of protein molecules embedded in it, separating these two compartments. Electrical balance is provided by concentration gradients which are maintained by a combination of selective permeability characteristics and active pumping mechanism.

The lipid component of the membrane is a double sheet of phospholipids, elongated molecules with polar groups at one end and the fatty acid chains at the other. The ions that carry the currents used for neuronal signaling are among these water-soluble substances, so the lipid bilayer is also an insulator, across which membrane potentials develop. In biophysical terms, the lipid bilayer is not permeable to ions. In electrical terms, it functions as a capacitor, able to store charges of opposite sign that are attracted to each other but unable to cross the membrane. Embedded in the lipid bilayer is a large assortment of proteins. These are proteins that regulate the passage of ions into or out of the cell. Certain membrane-spanning proteins allow selected ions to flow down electrical or concentration gradients or by pumping them across.

These membrane-spanning proteins consist of several subunits surrounding a central aqueous pore. Ions whose size and charge "fit" the pore can diffuse through it, allowing these proteins to serve as ion channels. Hence, unlike the lipid bilayer, ion channels have an appreciable permeability (or conductance) to at least some ions. In electrical terms, they function as resistors, allowing a predicable amount of current flow in response to a voltage across them.

A nerve fiber can be excited by increasing the electrical charge within the neuron, thus increasing the membrane potential inside the nerve with respect to the surrounding extracellular fluid. The threshold stimulus intensity is defined as that value at which the net inward current (which is largely determined by Sodium ions) is just greater than the net outward current (which is largely carried by Potassium ions), and is typically around −55 mV inside the nerve cell relative to the outside (critical firing threshold). If however, the threshold is not reached, the graded depolarization will not generate an action potential and the signal will not be propagated along the axon. This fundamental feature of the nervous system i.e., its ability to generate and conduct electrical impulses, can take the form of action potentials, which are defined as a single electrical impulse passing down an axon. This action potential (nerve impulse or spike) is an "all or nothing" phenomenon, that is to say once the threshold stimulus intensity is reached, an action potential will be generated.

FIG. 8A illustrates a segment of the surface of the membrane of an excitable cell. Metabolic activity maintains ionic gradients across the membrane, resulting in a high concentration of potassium ($K^+$) ions inside the cell and a high concentration of sodium ($Na^+$) ions in the extracellular environment. The net result of the ionic gradient is a transmembrane potential that is largely dependent on the $K^+$ gradient. Typically in nerve cells, the resting membrane potential (RMP) is slightly less than 90 mV, with the outside being positive with respect to inside.

To stimulate an excitable cell, it is only necessary to reduce the transmembrane potential by a critical amount. When the membrane potential is reduced by an amount $\Delta V$, reaching the critical or threshold potential (TP); Which is shown in FIG. 8B. When the threshold potential (TP) is reached, a regenerative process takes place: sodium ions enter the cell, potassium ions exit the cell, and the transmembrane potential falls to zero (depolarizes), reverses slightly, and then recovers or repolarizes to the resting membrane potential (RMP).

For a stimulus to be effective in producing an excitation, it must have an abrupt onset, be intense enough, and last long enough. These facts can be drawn together by considering the delivery of a suddenly rising cathodal constant-current stimulus of duration d to the cell membrane as shown in FIG. 8B. Cell membranes can be reasonably well represented by a capacitance C, shunted by a resistance R as shown by a simplified electrical model in diagram 8C.

When the stimulation pulse is strong enough, an action potential will be generated and propagated. Immediately after the spike of the action potential there is a refractory period when the neuron is either unexcitable (absolute refractory period) or only activated to sub-maximal responses by supra-threshold stimuli (relative refractory period). The absolute refractory period occurs at the time of maximal Sodium channel inactivation while the relative refractory period occurs at a later time when most of the $Na^+$ channels have returned to their resting state by the voltage activated $K^+$ current. The refractory period has two important implications for action potential generation and conduction. First, action potentials can be conducted only in one direction, away from the site of its generation, and secondly, they can be generated only up to certain limiting frequencies.

These electrical signals travel along the nerve fibers. The information in the nervous system is coded by frequency of firing rather than the size of the action potential. In terms of electrical conduction, myelinated fibers conduct faster, are typically larger, have very low stimulation thresholds, and exhibit a particular strength-duration curve or respond to a specific pulse width versus amplitude for stimulation, compared to unmyelinated fibers. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Because of their very slow conduction, C fibers would not be highly responsive to rapid stimulation. Selective stimulation of only A and B fibers is readily accomplished. The requirement of a larger and wider pulse to stimulate the C fibers, however, makes selective stimulation of only C fibers, to the exclusion of the A and B fibers, virtually unachievable in as much as the large signal will tend to activate the A and B fibers to some extent as well.

As shown in FIG. 9, when the distal part of a nerve is electrically stimulated, a compound action potential is recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories as shown in the Table one below,

TABLE 1

| Fiber Type | Conduction Velocity (m/sec) | Fiber Diameter (μm) | Myelination |
| --- | --- | --- | --- |
| A Fibers | | | |
| Alpha | 70–120 | 12–20 | Yes |
| Beta | 40–70 | 5–12 | Yes |
| Gamma | 10–50 | 3–6 | Yes |
| Delta | 6–30 | 2–5 | Yes |
| B Fibers | 5–15 | <3 | Yes |
| C Fibers | 0.5–2.0 | 0.4–1.2 | No |

For many of the applications of current patent application, it is the slow conduction C-fibers that are stimulated by the pulse generator. The modulation of nerve in the periphery, as done by the body, in response to different types of pain is illustrated schematically in FIGS. 10 and 11. As shown schematically in FIG. 10, the electrical impulses in response to acute pain sensations are transmitted to brain through peripheral nerve and the spinal cord. The first-order peripheral neurons at the point of injury transmit a signal along A-type nerve fibers to the dorsal horns of the spinal cord. Here the second-order neurons take over, transfer the signal to the other side of the spinal cord, and pass it through the spinothalamic tracts to thalamus of the brain. Of relevance to most therapy applications, and as shown in FIG. 11, duller and more persistent pain travels by another-slower route using unmyelinated C-fibers. This route made up from a chain of interconnected neurons, which run up the spinal cord to connect with the brainstem, the thalamus and finally the cerebral cortex. The autonomic nervous system also senses pain and transmits signals to the brain using a similar route to that for dull pain.

Vagus nerve stimulation, as performed by the system and method of the current patent application, is a means of directly affecting central function. Cranial nerves have both afferent pathway 19 (inward conducting nerve fibers which convey impulses toward the brain) and efferent pathway 21 (outward conducting nerve fibers which convey impulses to an effector), shown in FIG. 11B. Vagus nerve is composed of 80% afferent sensory fibers carrying information from the head, neck, thorax, and abdomen to the brain. The sensory afferent cell bodies of the vagus reside in the nodose ganglion and relay information to the nucleus tractus solitarius (NTS).

The vagus nerve is composed of somatic and visceral afferents and efferents. Usually, nerve stimulation activates signals in both directions (bi-directionally). It is possible however, through the use of special electrodes and waveforms, to selectively stimulate a nerve in one direction only (unidirectionally). The vast majority of vagus nerve fibers are C fibers, and a majority are visceral afferents having cell bodies lying in masses or ganglia in the skull.

In considering the anatomy, the vagus nerve spans from the brain stem all the way to the splenic flexure of the colon. Not only is the vagus the parasympathetic nerve to the thoracic and abdominal viscera, it also the largest visceral sensory (afferent) nerve. Sensory fibers outnumber parasympathetic fibers four to one. In the medulla, the vagal fibers are connected to the nucleus of the tractus solitarius (viceral sensory), and three other nuclei. The central projections terminate largely in the nucleus of the solitary tract, which sends fibers to various regions of the brain (e.g., the thalamus, hypothalamus and amygdala).

As shown in FIG. 12, the vagus nerve emerges from the medulla of the brain stem dorsal to the olive as eight to ten rootlets. These rootlets converge into a flat cord that exits the skull through the jugular foramen. Exiting the Jugular foramen, the vagus nerve enlarges into a second swelling, the inferior ganglion.

In the neck, the vagus lies in a groove between the internal jugular vein and the internal carotid artery. It descends vertically within the carotid sheath, giving off branches to the pharynx, larynx, and constrictor muscles. From the root of the neck downward, the vagus nerve takes a different path on each side of the body to reach the cardiac, pulmonary, and esophageal plexus (consisting of both sympathetic and parasympathetic axons). From the esophageal plexus, right and left gastric nerves arise to supply the abdominal viscera as far caudal as the splenic flexure.

In the body, the vagus nerve regulates viscera, swallowing, speech, and taste. It has sensory, motor, and parasympathetic components. Table two below outlines the innervation and function of these components.

TABLE 2

| Vagus Nerve Components | | |
| --- | --- | --- |
| Component fibers | Structures innervated | Functions |
| SENSORY | Pharynx. larynx, esophagus, external ear | General sensation |
| | Aortic bodies, aortic arch Thoracic and abdominal viscera | Chemo- and baroreception |
| MOTOR | Soft palate, pharynx, larynx, upper esophagus | Speech, swallowing |
| PARASYMPATHETIC | Thoracic and abdominal viscera | Control of cardiovascular system, respiratory and gastrointestinal tracts |

On the Afferent side, visceral sensation is carried in the visceral sensory component of the vagus nerve. As shown in FIGS. 13 and 14, visceral sensory fibers from plexus around the abdominal viscera converge and join with the right and left gastric nerves of the vagus. These nerves pass upward through the esophageal hiatus (opening) of the diaphragm to merge with the plexus of nerves around the esophagus. Sensory fibers from plexus around the heart and lungs also converge with the esophageal plexus and continue up through the thorax in the right and left vagus nerves. As shown in FIG. 14, the central process of the nerve cell bodies in the inferior vagal ganglion enter the medulla and descend in the tractus solitarius to enter the caudal part of the nucleus of the tractus solitarius. From the nucleus, bilateral connections important in the reflex control of cardiovascular, respiratory, and gastrointestinal functions are made with several areas of the reticular formation and the hypothalamus.

The afferent fibers project primarily to the nucleus of the solitary tract (shown schematically in FIGS. 15 and 16) which extends throughout the length of the medulla oblongata. A small number of fibers pass directly to the spinal trigeminal nucleus and the reticular formation. As shown in FIG. 15, the nucleus of the solitary tract has widespread projections to cerebral cortex, basal forebrain, thalamus, hypothalamus, amygdala, hippocampus, dorsal raphe, and cerebellum. Because of the widespread projections of the Nucleus of the Solitary Tract, neuromodulation of the vagal afferent nerve fibers produce alleviation of symptoms of the neurological and neuropsychiatric disorders covered in this patent application.

The system and methods disclosed herein also may be appropriate for the treatment of other conditions, as disclosed in a co-pending application filed on May 11, 2003 entitled, METHOD AND SYSTEM FOR PROVIDING PULSED ELECTRICAL STIMULATION TO A SACRAL NERVE OF A PATIENT FOR PROVIDING THERAPY FOR URINARY INCONTINENCE AND UROLOGICAL DISORDERS, the disclosure of which is incorporated herein by reference.

SUMMARY OF THE INVENTION

The current invention discloses a method and system for neuromodulating a cranial nerve with an implantable stimulator, to provide therapy for neurological and neuropsychiatric disorders. The implantable stimulator of the current invention comprising a pulse generator module and a stimulus receiver module for coupling with an external stimulator.

One object of the present invention is to provide an improved system and method for pulsed electrical stimulation to provide therapy for neurological and neuropsychiatric disorders. Another object is to derive at the optimal pulsed electrical stimulation dose for the individual patient in a convenient way, where an attending physician can activate (or de-activate) the therapy program remotely. A further object is to extend the service life of the implanted stimulator, whereby more intensive therapy can be given if appropriate, and surgical interventions for replacement of implanted stimulators are reduced.

Accordingly in one aspect of the invention, the system comprises an implantable stimulator and a lead, an external stimulator, and a programmer. The implantable stimulator comprising a pulse generator module deriving power from an implanted battery, and a stimulus receiver module deriving power from an external stimulator. Control circuitry ensures selective operation of one pulse generator module. The implanted pulse generator module delivering electric stimulation therapy to a vagus nerve according to pre-determined parameters programmed by the programmer. The implanted stimulator system operates according to a program stored in the memory. Upon receiving stimulus energy from an inductively coupled external stimulator, the implanted pulse generator goes into "sleep" mode. The length of time that the internal battery operated pulse generator stays in "sleep" mode is a programmable parameter.

In another aspect of the invention, the external stimulator is adapted to be remotely controllable via the internet. The external stimulator comprises a number of predetermined programs. Several of these programs are locked out to the patient, and can be activated (or de-activated) remotely via the internet, by the medical staff. Since each patient is unique, different stimulation parameters can be tried by the patient, without the patient having to travel to the clinic for programming. Once the optimal stimulation therapy program is identified, the patient can have the implanted stimulator programmed to the optimal settings.

In another aspect of the invention, the external stimulator may be used in conjunction with the implanted stimulus receiver in order to extend the service life of the implantable stimulator or to temporarily deliver more aggressive therapy for specific situations.

In another aspect of the invention, with some modification in the circuitry, the implantable stimulator may be used as a re-chargable implantable pulse generator to provide therapy for neurological and neuropsychiatric disorders.

In yet another aspect of the invention the implantable stimulator may be programmerless, whereby limited programmability can be realized with a magnet.

In another aspect of the invention, the external stimulator comprises a telemetry module and is adapted to be networked.

In yet another aspect of the invention, the programmer or the external stimulator comprises a global positioning system (GPS) module for patient location.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 7 is a diagram showing different types of nerve fibers.

FIGS. 8A, 8B, 8C are schematic illustrations of the electrical properties of nerve cell membrane.

FIG. 9 is a diagram showing recordings of compound action potentials.

FIGS. 19A and 19B show assembly features of the implantable portion of the system.

FIGS. 23A and 23B diagrammatically represents encoding and decoding of programming pulses.

FIG. 32A is diagram depicting stimulating electrode-tissue interface.

FIG. 32B is diagram depicting electrical model of the electrode-tissue interface.

DETAILED DESCRIPTION OF THE INVENTION

The following description is of the current embodiment for carrying out the invention. This description is not to be taken in a limiting sense, but is made merely for the purpose of describing the general principles of the invention.

Figure 1:
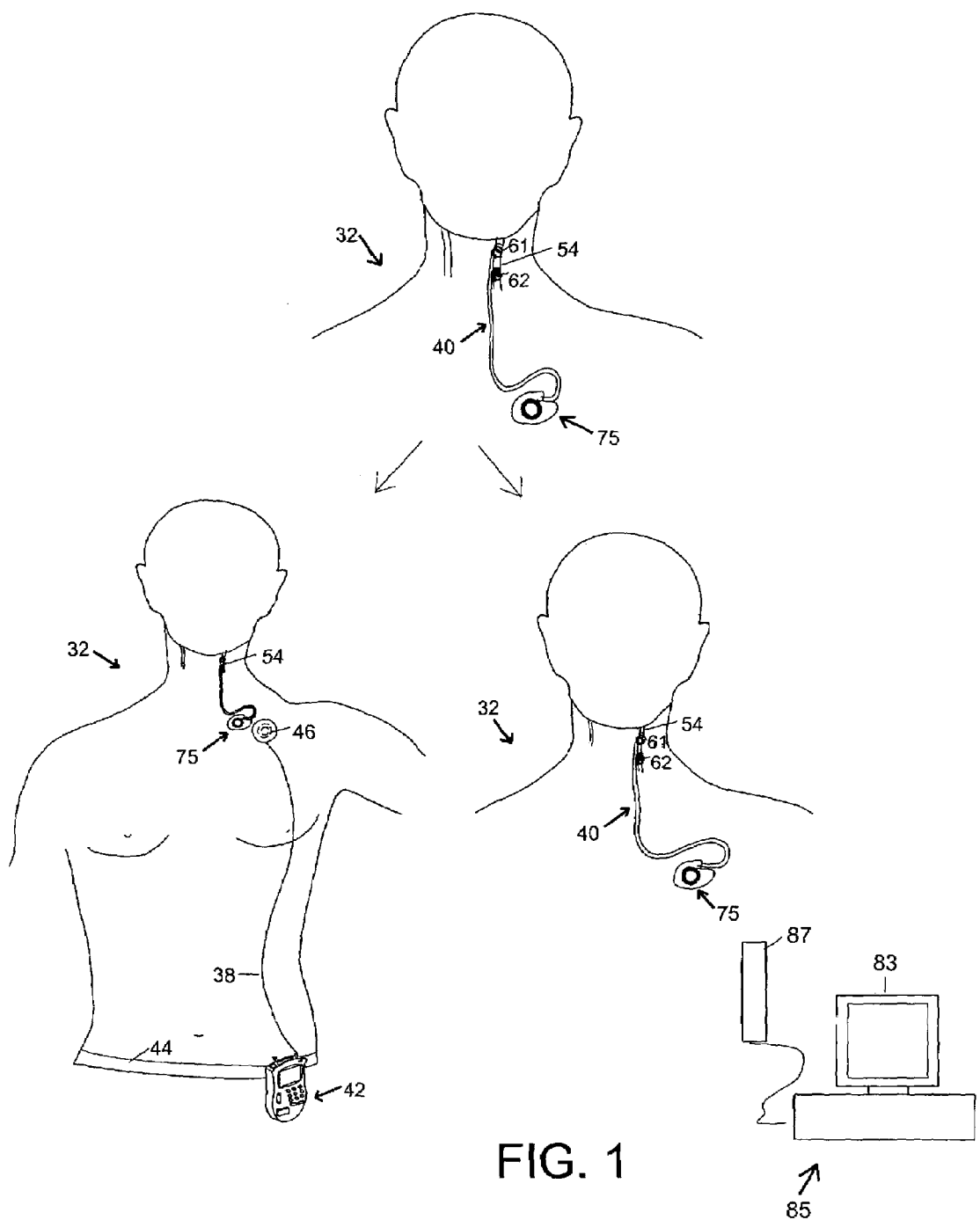
FIG. 1 diagrammatically illustrates the concept of an IPG being used with an external stimulator or a programmer.

As shown in FIG. 1, the system of the present invention comprises, an implanted stimulator 75, an implanted lead 40, an external stimulator 42, and an external programmer 85.

Figure 2:
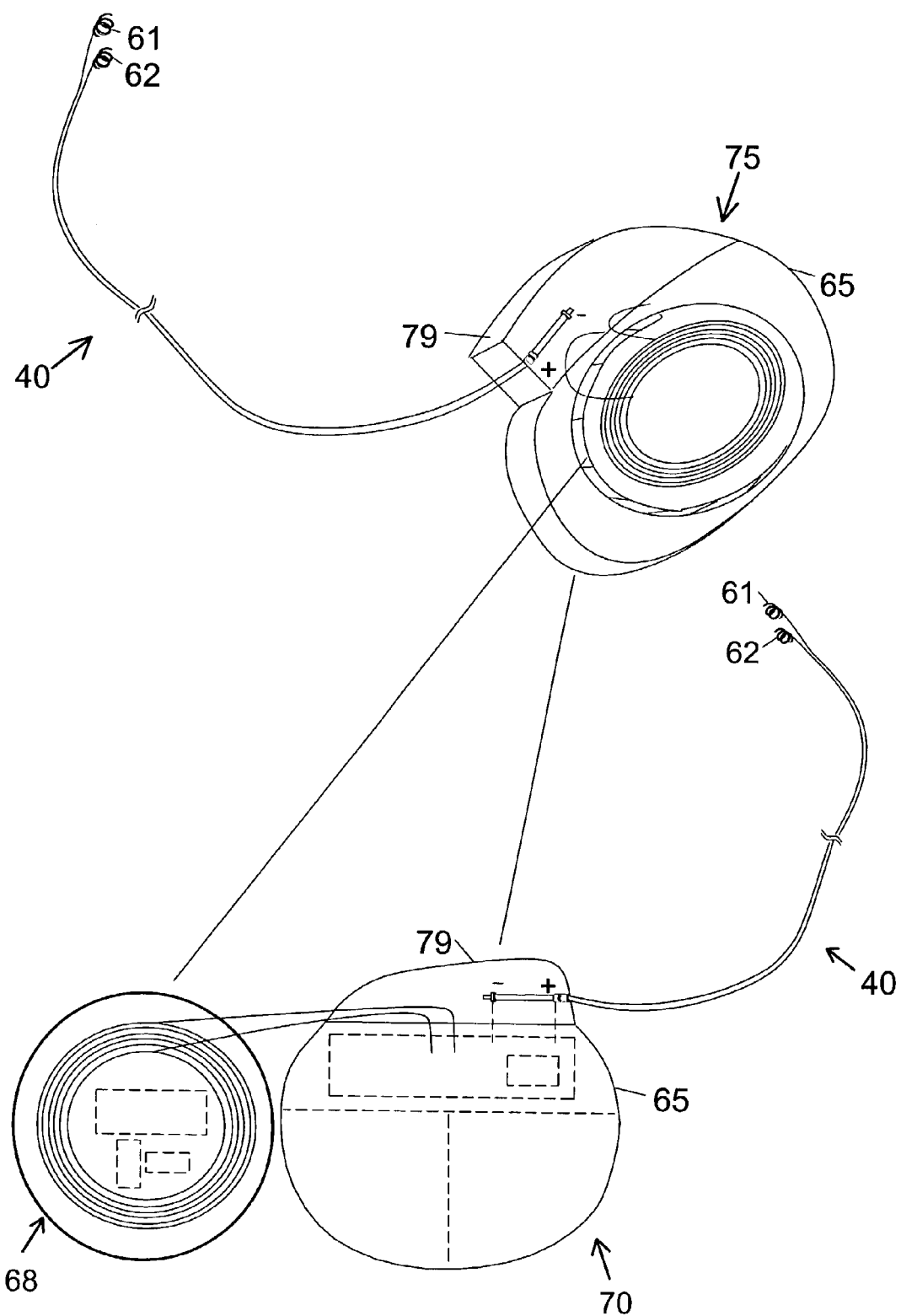
FIG. 2 is a diagram showing the implantable components of the system.

As is shown in FIG. 2, the implantable stimulator 75 contains two stimulator assemblies 68,70 which operate in a coordinated fashion because of the control circuitry coordinating the two assemblies. The stimulus receiver module 68, which is outside (or may be inside) of the titanium can 65 is similar to an inductively coupled stimulation system, known in the art as "RF Neurostimulation System". The second assembly, which is encased in a titanium can 65 is the implanted pulse generator (IPG) deriving power from an implanted battery. Control circuitry ensures that the two assemblies operate correctly.

Figure 17A:
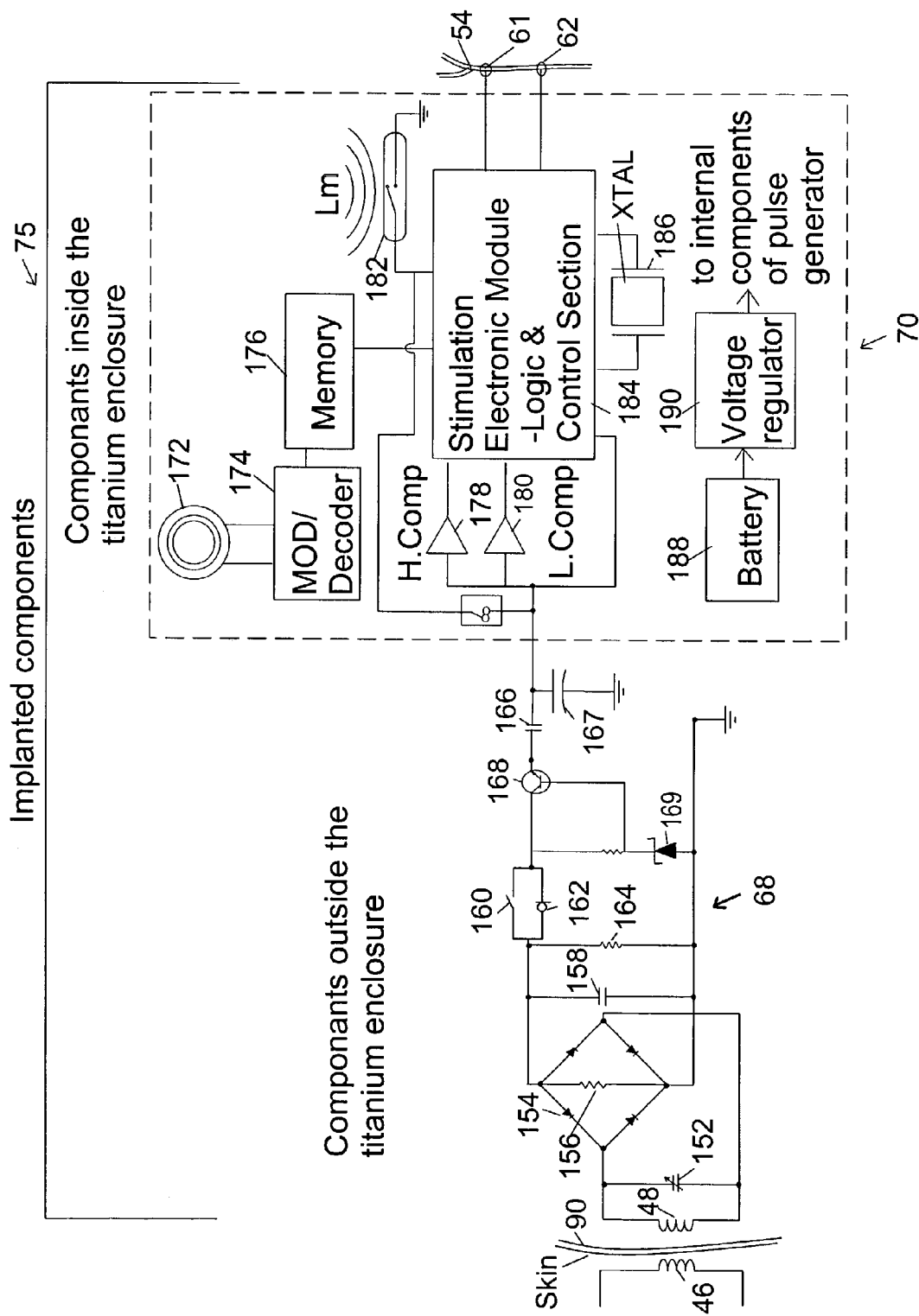
FIG. 17A is a schematic and functional block diagram showing the components and their relationships to the implantable pulse generator.

A simplified schematic and block diagram of the implantable stimulator 75 is shown in FIG. 17A. The inductively coupled stimulus receiver module 68 is shown in left part of the diagram in FIG. 17A. The battery operated portion 70 is shown on right side of the diagram. Much of the circuitry included within this embodiment of the stimulator 70 is realized on single application specific integrated circuit (ASIC). This allows the overall size of the IPG 70, to be quite small and readily housed within a suitable hermetically-sealed case, such as one made of titanium. Using CMOS technology and monolithic design, the analog and digital functions are integrated on a silicon chip approximately 5 mm×5 mm in size. Hybrid technology being used as a reliable connection technology for the wiring of the IC with non-integrated discrete components (like quartz oscillators, tantalum capacitors, coils of transmission, reed contacts, etc).

The implantable stimulator 75 is implanted in a patient, in the usual fashion by making an incision on the chest, and a second smaller incision in the neck to expose the vagus nerve for the placement of the electrodes 61, 62 around the vagus nerve. It is also known in the art that other cranial nerves (such as the trigeminal nerve) may be used for the same purpose. The lead 40 (shown in FIGS. 1 and 31) is tunneled subcutaneously, such that at the distal end the two stimulating electrodes 61, 62 are by the nerve to be stimulated, and the proximal end of the lead 40 is connected to the header 79 of the stimulator 75. The incisions are closed in the usual manner and stimulation can begin after the tissues are healed (approximately 2 weeks).

Once implanted, in the system and method of this invention, pulsed electrical stimulation can be performed either via an external stimulator 42 in conjunction with the stimulus receiver module 68, or via the implanted pulse generator 70 according to parameters which are programmed via an external programmer 85.

In one aspect of the invention, the physician can asses the stimulation parameters in terms of efficacy and tolerability to the patient, by using the external stimulator 42 in conjunction with the stimulus receiver module 68. Advantageously, the external stimulator 42 is networked, and can be controlled by a physician via the internet, from a distant location. Once the optimal stimulation parameters are assessed and the stimulation dose is "titrated", the stimulation parameters can by programmed into the implanted pulse generator 70 using the external programmer 85.

The "tuning" of the vagus nerve 54 (or another cranial nerve), for a particular patient, can be performed in one of two ways with the external stimulator 42. One method is to activate one of several "pre-determined" programs. A second method is to "custom" program the electrical parameters which can be selectively programmed, for specific disease state of the individual patient. The electrical parameters that can be individually programmed, include variables such as pulse amplitude, pulse width, pulses per second, modulation type, modulation index, stimulation on-time, and stimulation off-time.

The system of the present invention is designed such that when stimulation is applied via the external stimulator 42 through the primary (external) coil 46, and is picked up by the implanted (secondary) coil 48, the battery operated stimulation module (IPG) 70 is temporarily suspended. This is accomplished through the comparator circuitry 178, 180 which sends a control signal to the controller 184, causing the battery operated stimulator module to suspend operation and go to "sleep mode". The length of time for this "sleep mode" is programmable with the external programmer 85.

The external stimulator 42 comprises numerous (say 200) pre-packaged programs. In addition, "customized" programs can be generated and stored in one of the several memories available in the external stimulator 42. New programs can be loaded into the external stimulator 42, preferably as described in U.S. Pat. No. 6,366,814 B1, incorporated herein by reference. Each pre-packaged program comprises a unique combination of electrical pulse stimulation parameters such as pulse amplitude, pulse width, number of pulses per second, on-time and off-time. An example of a mild stimulation may be Program #1:

0.50 mA current output, 0.2 msec pulse width, 15 Hz frequency, 15 sec ON time-1.0 min OFF time, in repeating cycles.

Program #2:

1.0 mA current output, 0.3 msec pulse width, 20 Hz frequency, 20 sec ON time-2.0 min OFF time, in repeating cycles.

The following are examples of intermediate level of therapy.

Program #5:

2.0 mA current output, 0.2 msec pulse width, 25 Hz frequency, 20 sec ON time-1.0 min OFF time, in repeating cycles.

Program #6:

2.0 mA current output, 0.25 msec pulse width, 25 Hz frequency, 30 sec ON time-1.0 min OFF time, in repeating cycles.

The following are examples of most aggressive therapy.

Program #8:

2.5 mA current output, 0.3 msec pulse width, 30 Hz frequency, 40 sec ON time-1.5 min OFF time, in repeating cycles.

Program #9:

3.0 mA current output, 0.4 msec pulse width, 30 Hz frequency, 30 sec ON time-1.0 min OFF time, in repeating cycles.

In addition to the prepackaged programs, customized stimulation programs may be programmed from a range of parameters shown in Table 3.

TABLE 3

| Electrical parameter range delivered to the nerve | |
|---|---|
| PARAMER | RANGE |
| Pulse Amplitude | 0.1 Volt–10 Volts |
| Pulse width | 20 µS–5 mSec. |
| Frequency | 5 Hz–200 Hz |
| On-time | 10 Secs–24 hours |

TABLE 3-continued

| Electrical parameter range delivered to the nerve | |
|---|---|
| PARAMER | RANGE |
| Off-time | 10 Secs–24 hours |

The parameters in Table 3 are the electrical signals delivered to the nerve via the two electrodes 61,62 (distal and proximal) around the nerve, as shown in FIG. 17A. It being understood that the signals generated by the external stimulator and transmitted via the primary coil 46 (antenna) are larger, because the attenuation factor between the primary coil 46 and secondary coil 48 is approximately 10–20 times, depending upon the distance, and orientation between the two coils. Accordingly, the range of transmitted signals of the external pulse generator are approximately 10–20 times larger than shown in Table 3.

In the method and system of current invention, much of the stimulation parameters "dose" titration, and patient tolerability to "aggressive" stimulation can be performed without the patient having to go to the clinic or physician's office for programming. Many of the pre-packaged programs are initially locked out to the patient. During the course of therapy, the physician can selectively activate the few programs that the patient is going to try for evaluating efficacy of therapy and patient tolerance. The remote activation and de-activation of selected pre-packaged programs may be performed by the medical staff from a distant location using cable modem and internet, as described in a co-pending application Ser. No. 09/794,530. Alternatively, the medical staff can activate (and de-activate) selected pre-packaged programs over the wireless internet as disclosed in another co-pending application Ser. No. 09/837,565. Both of the disclosures being incorporated herein in their entirety by reference. Such activation and de-activation of selected pre-packaged programs may be used in "titrating" the optimal dose for therapy.

Patient tolerance to such nerve stimulation therapy can vary widely. Once the particular patient's tolerance and response is "characterized", the stimulation parameters can be programmed into the battery operated module of the implanted stimulator 75 via an external programmer 85.

Figure 3:
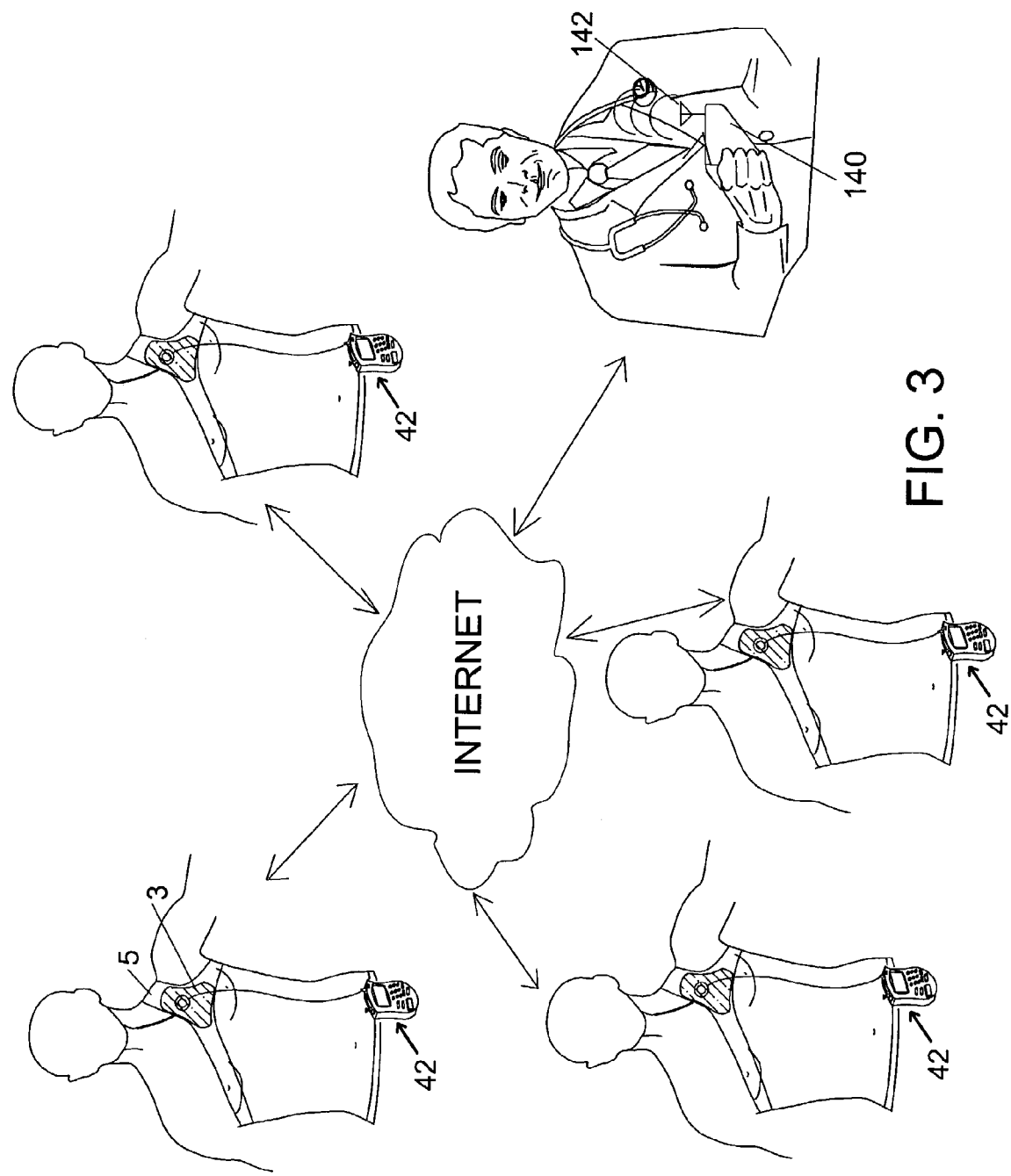
FIG. 3 shows diagrammatically physician's control of external stimulator device via the internet.
Figure 4A:
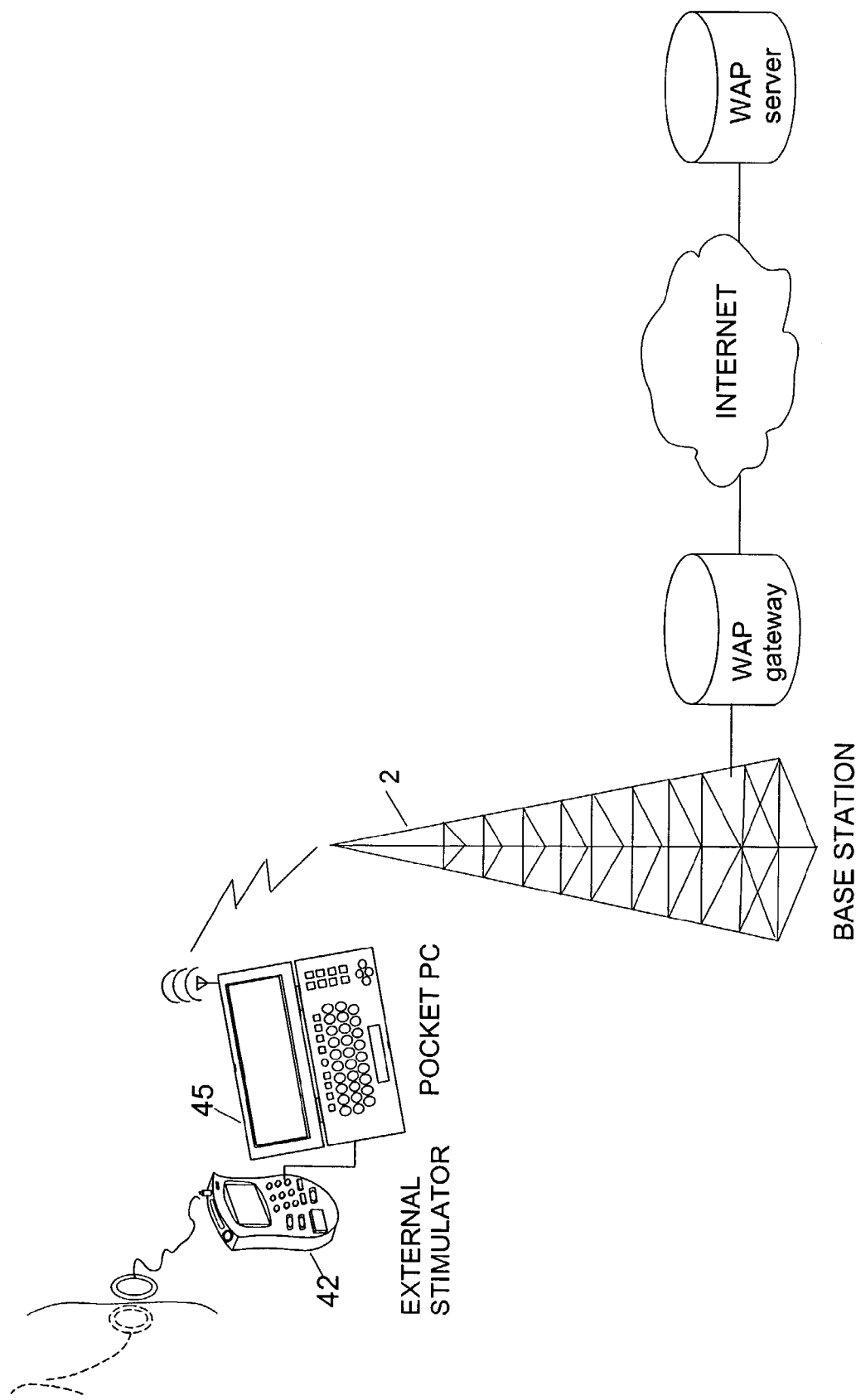
FIGS. 4A and 4B are diagrams showing communication of the external stimulator with the internet.
Figure 4B:
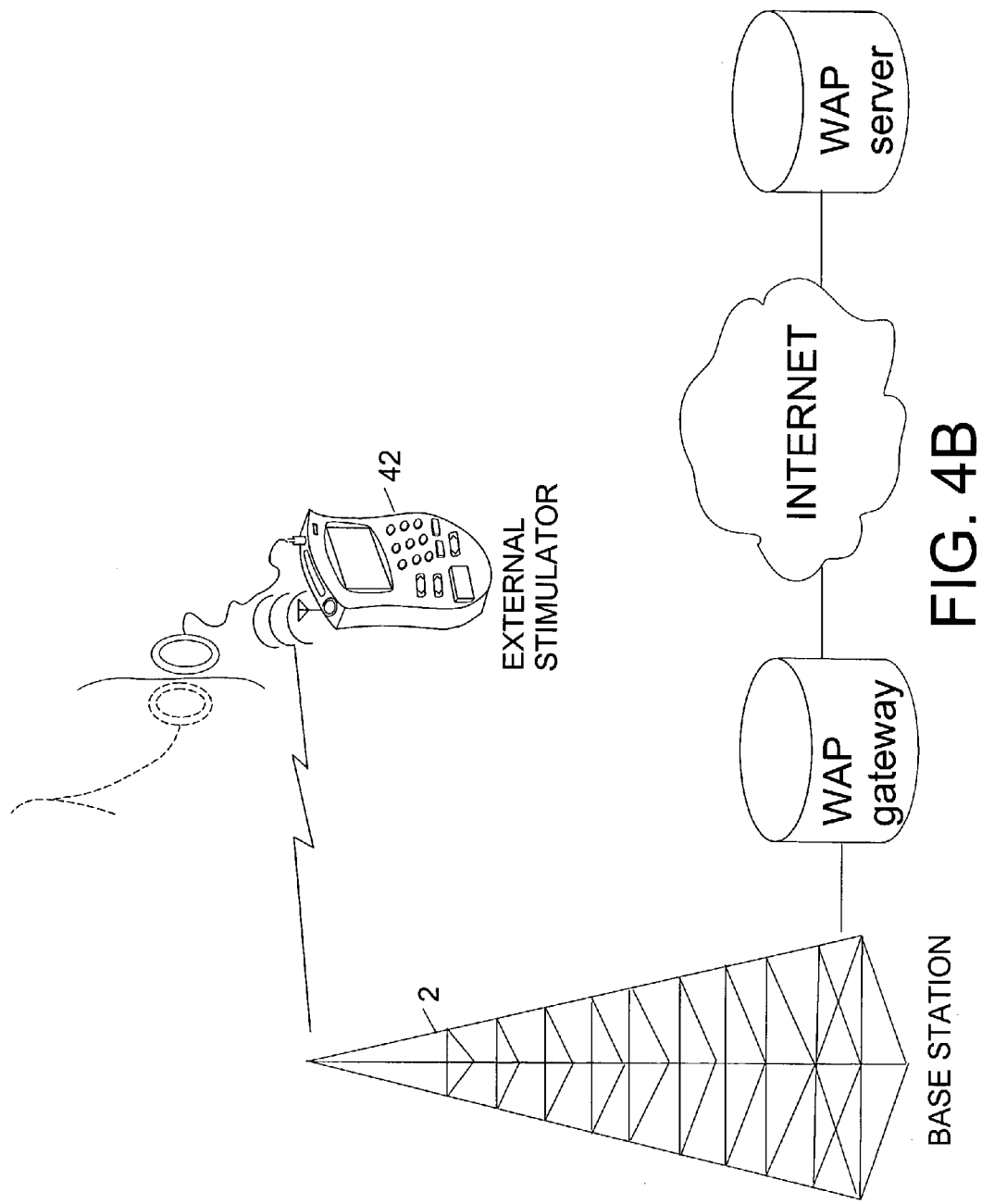
Figure 5:
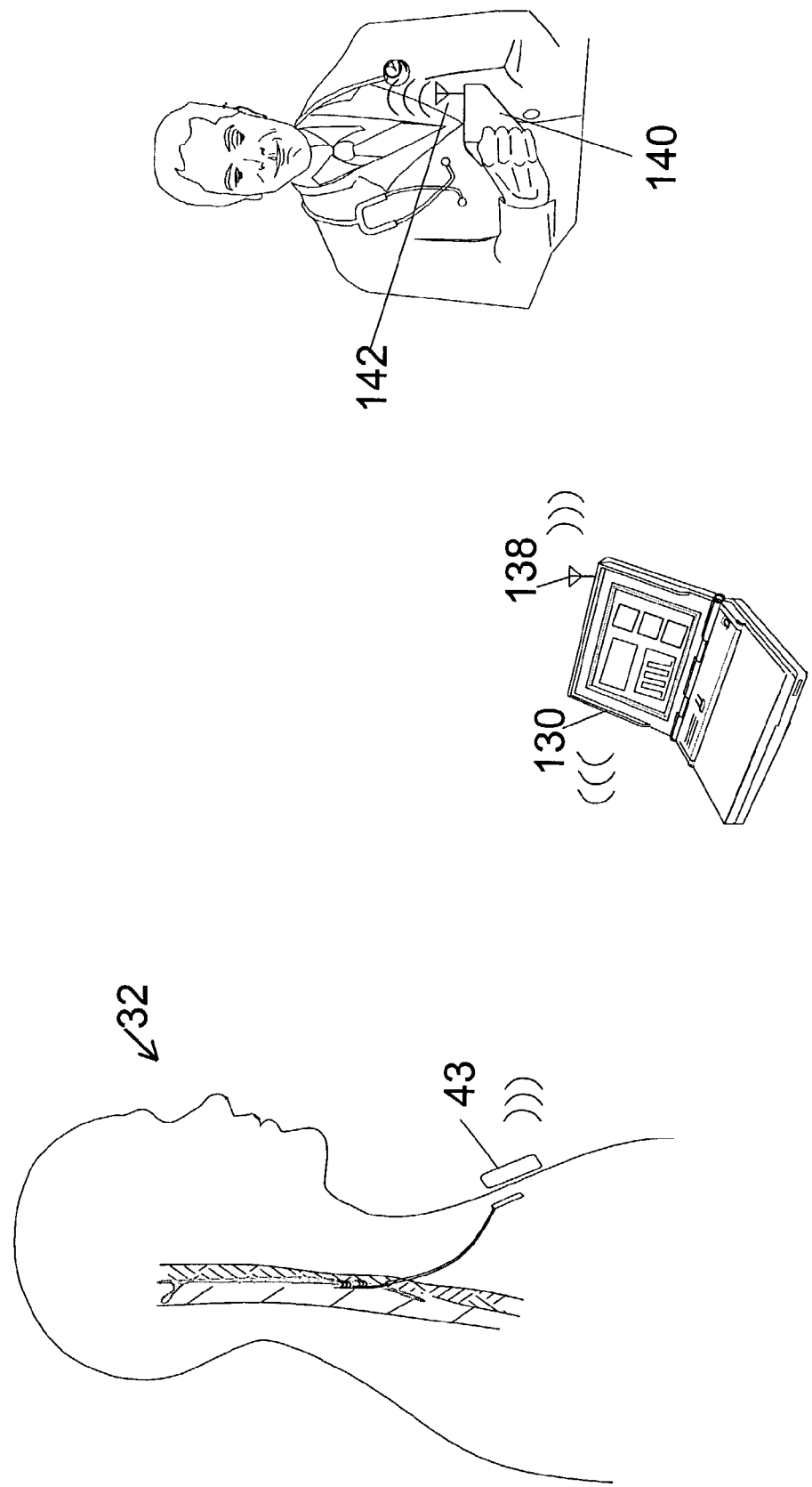
FIG. 5 is a diagram showing a physician communicating with a remote external stimulator from a hand-held device through a server.
Figure 6:
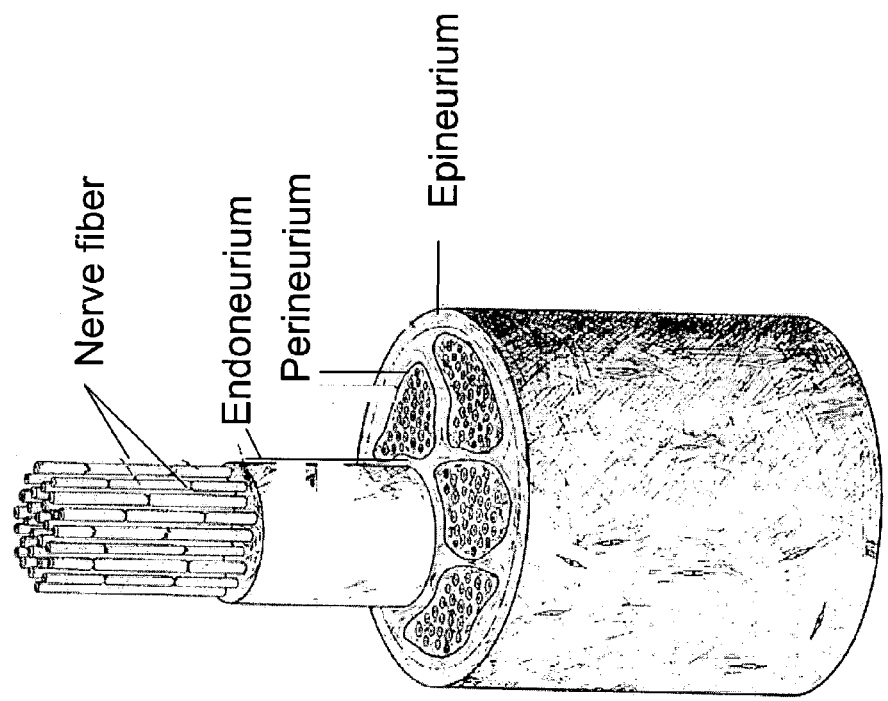
FIG. 6 is a diagram of the structure of a nerve.
Figure 10:
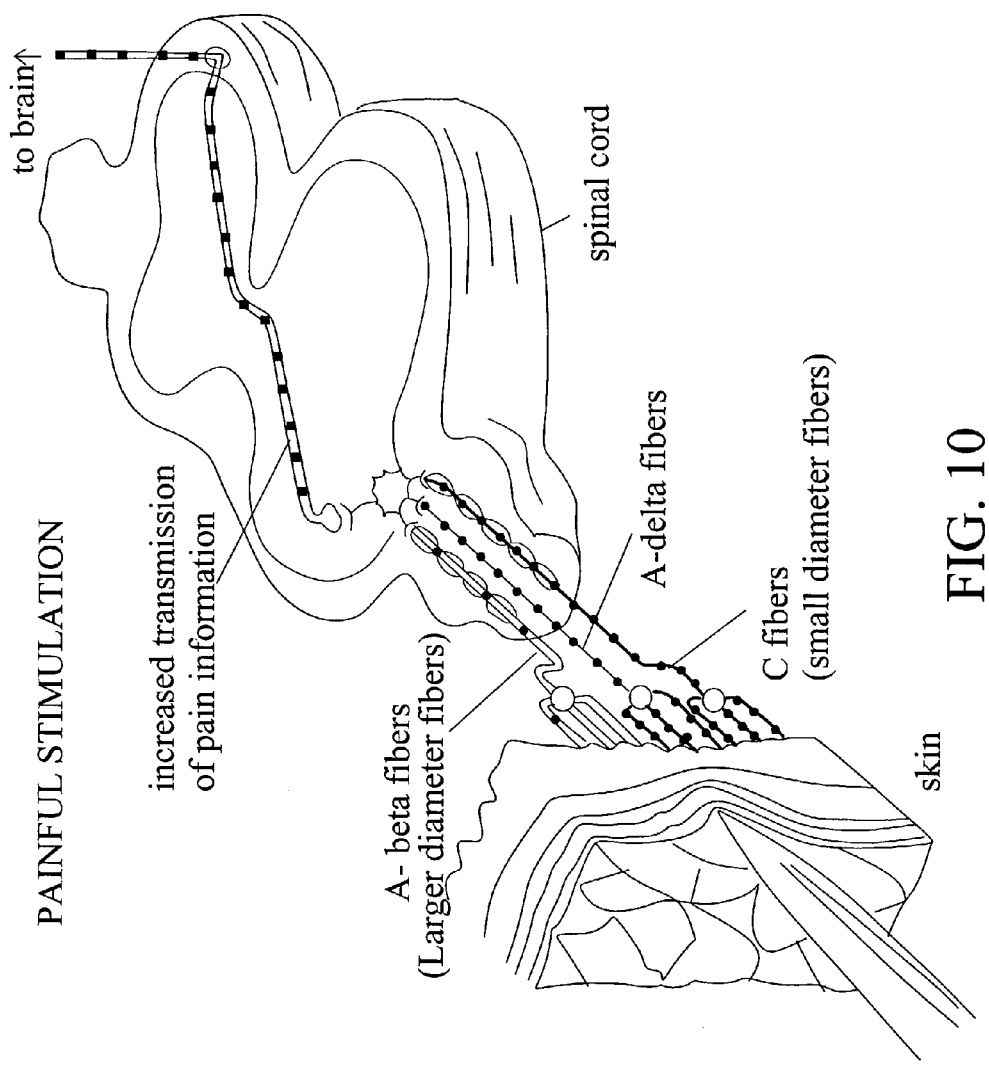
FIG. 10 is a schematic illustration, showing painful stimulation being carried over large diameter and small diameter fibers.
Figure 11:
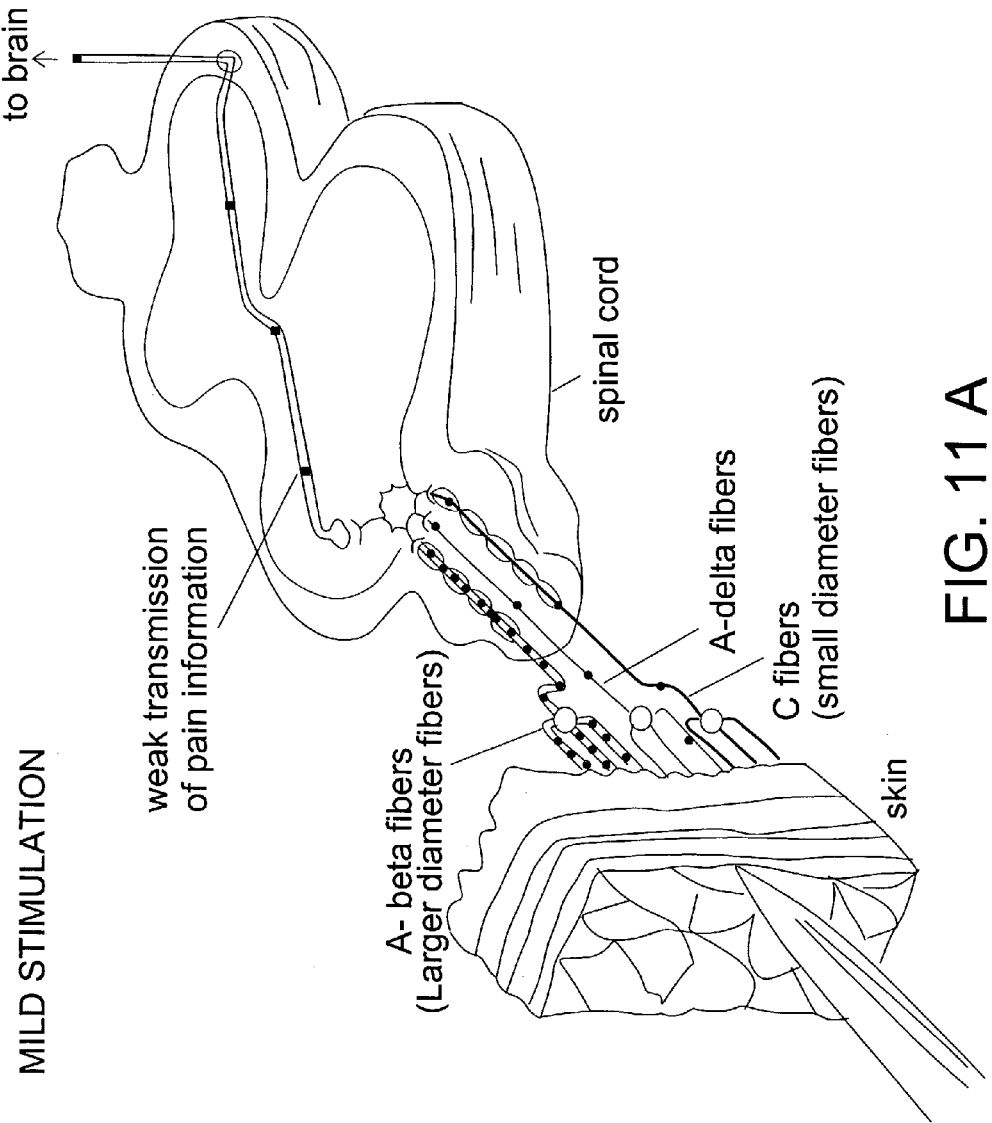
FIG. 11A is a schematic illustration, showing mild stimulation being carried over large diameter and small diameter fibers.
FIG. 11B is a schematic illustration showing afferent 19 and efferent 21 transmission.
Figure 11B:
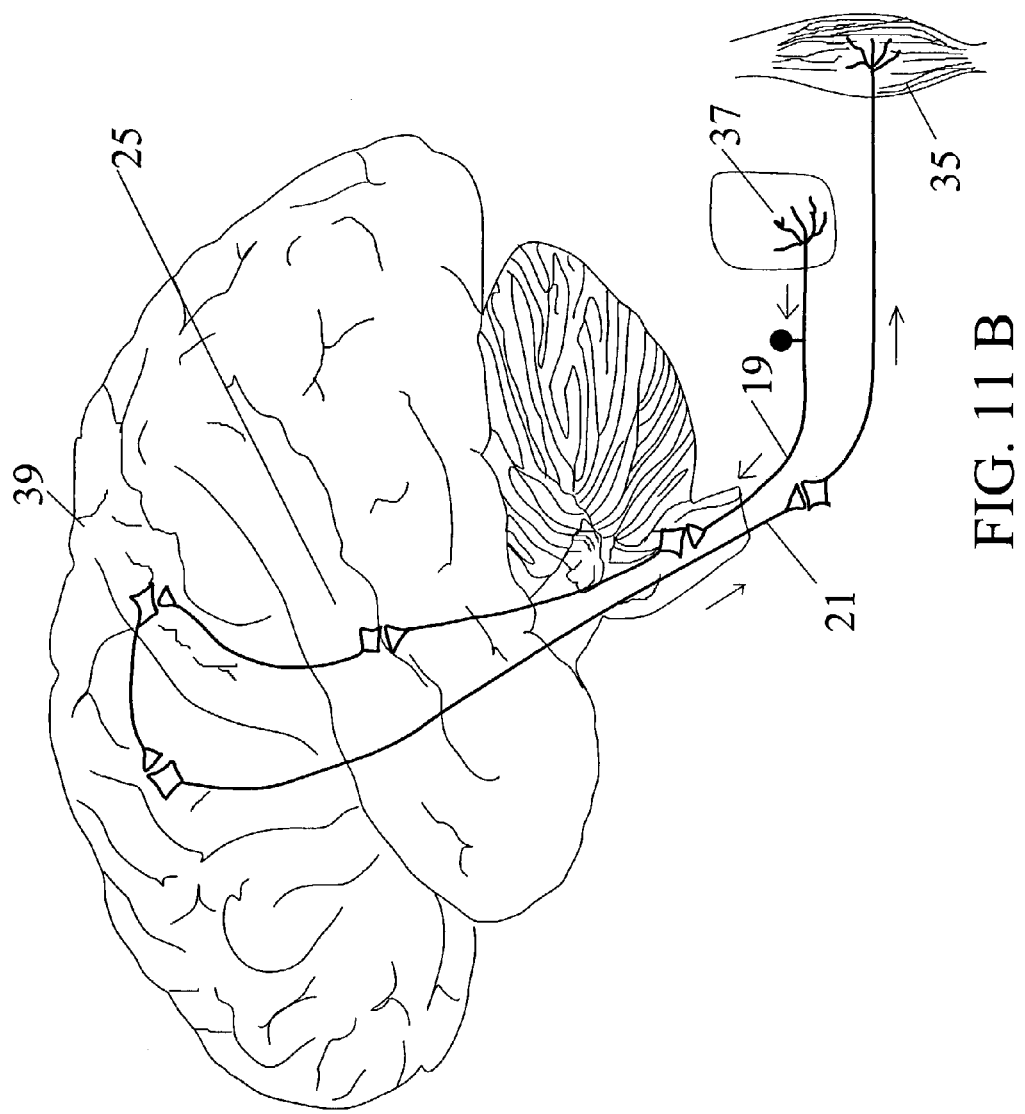
Figure 12:
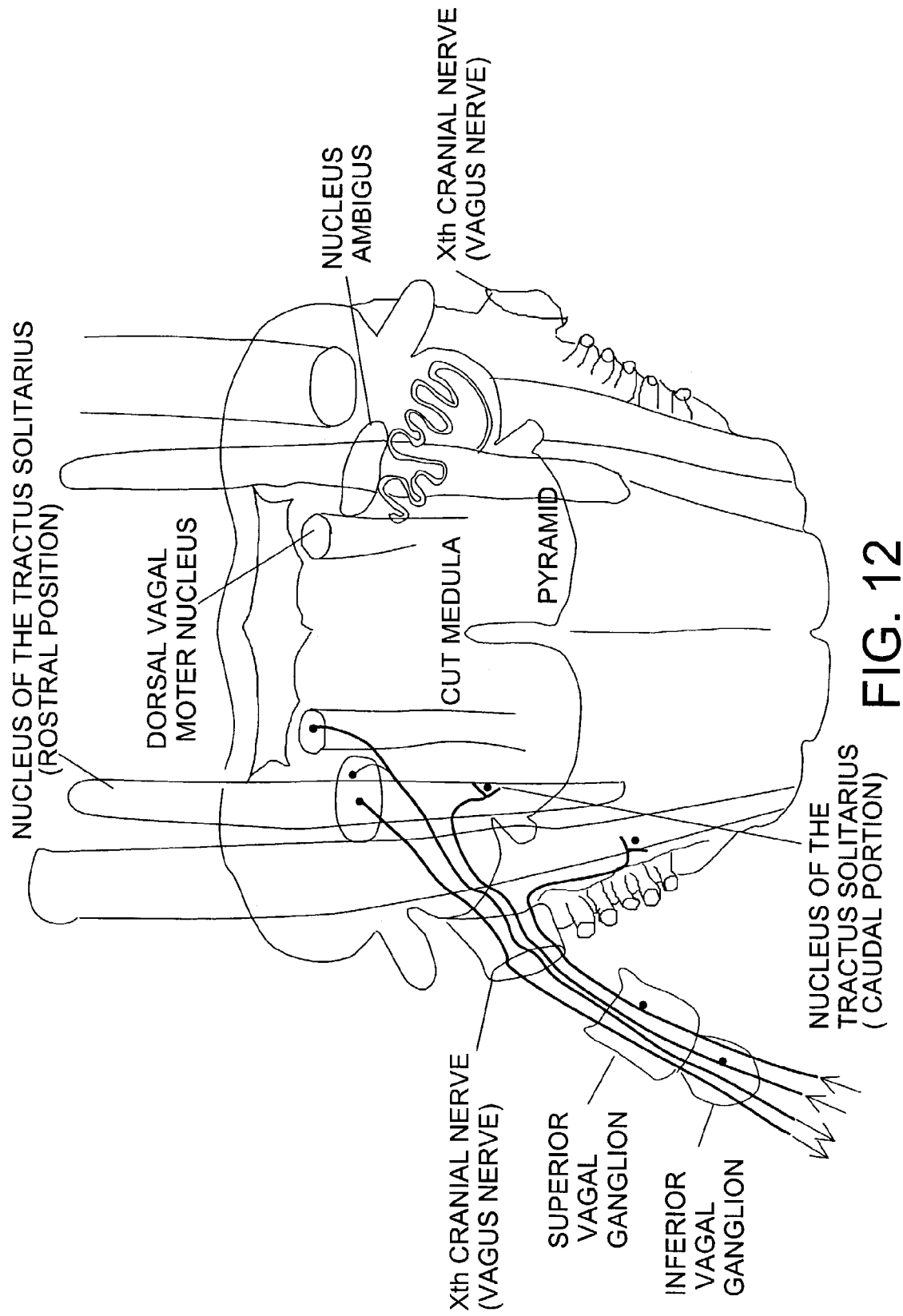
FIG. 12 is a schematic diagram showing the vagus nerve at the level of the nucleus of the solitary tract.
Figure 13:
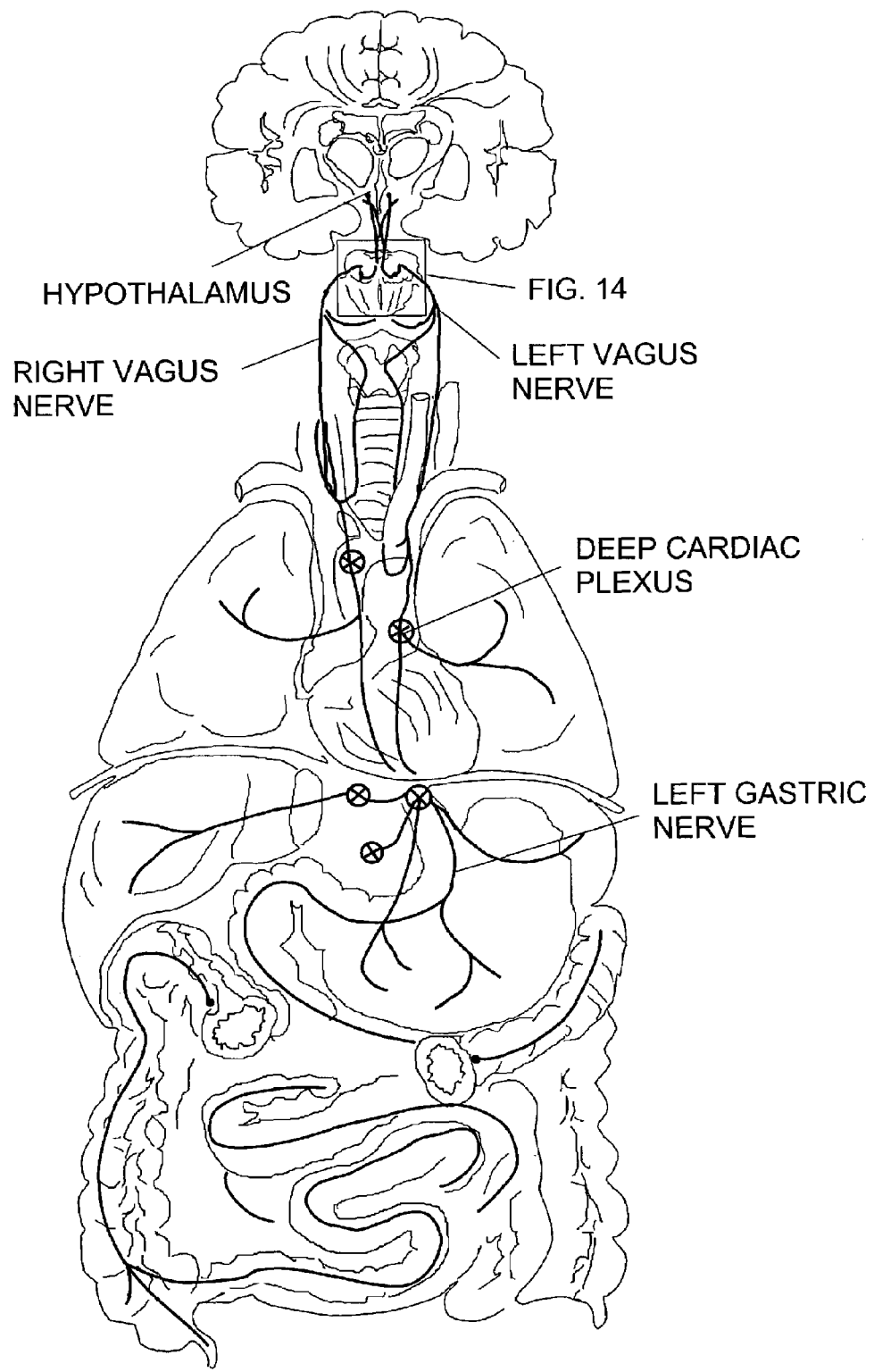
FIG. 13 is a schematic diagram showing the thoracic and visceral innervations of the vagal nerves.
Figure 14:
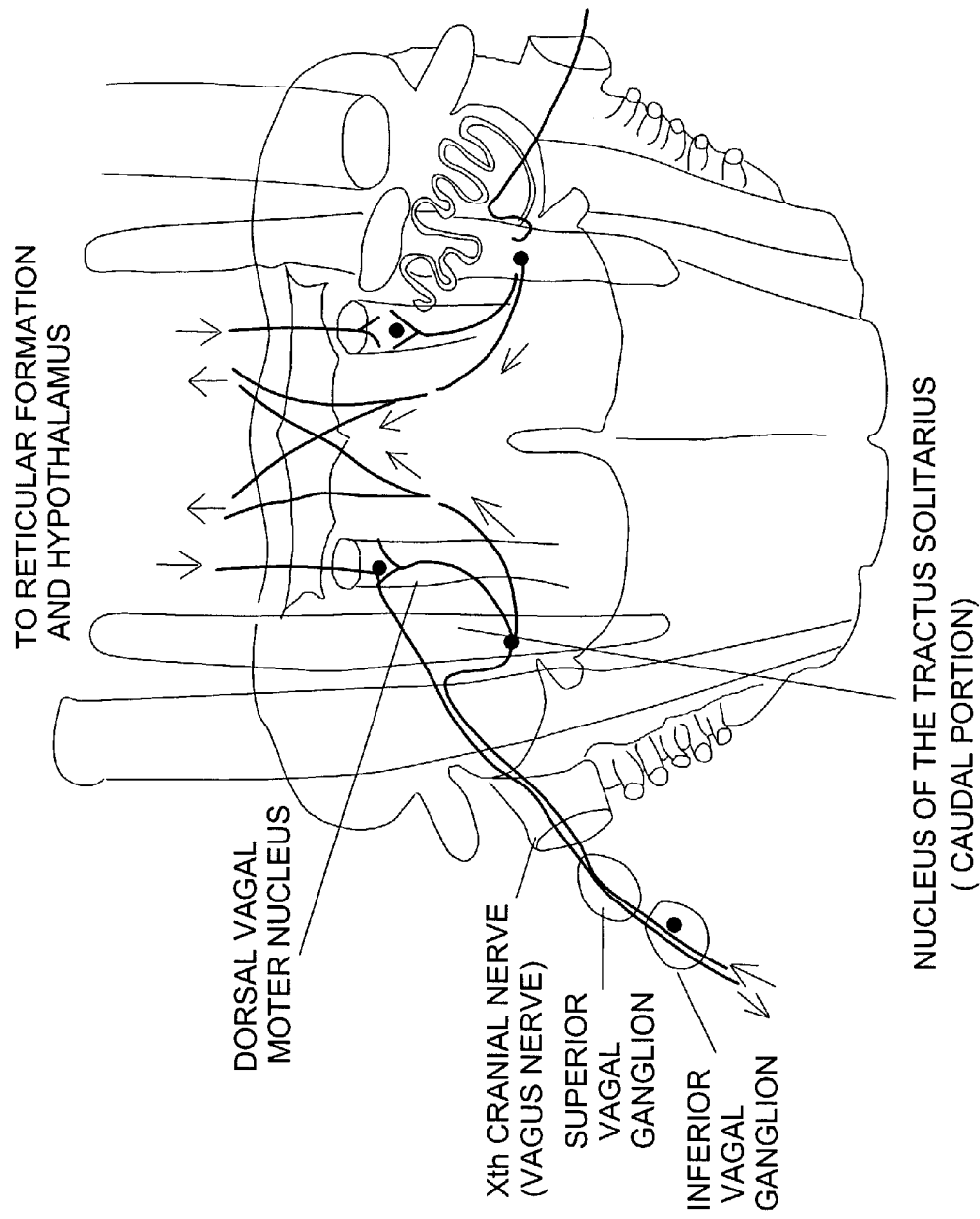
FIG. 14 is a schematic diagram of the medullary section of the brain.

With reference to FIG. 17A, for the functioning of the inductively coupled stimulus receiver 68, a primary (external) coil 46 is placed in close proximity to secondary (implanted) coil 48. As shown in FIG. 3, a custom designed garment 5 may be used for this purpose, or the primary coil 46 my be taped to skin. Referring to the left portion of FIG. 17A, the amplitude and pulse width modulated radiofrequency signals from the primary coil 46 are electromagnetically coupled to the secondary (implanted) coil 48 in the implanted unit 75. The two coils, 46 and 48 thus act like an air-gap transformer. The system having means for proximity sensing between the coils and feedback regulation of signals as described more fully in U.S. Pat. No. 6,473,652 B1, which is incorporated herein in its entirety by reference.

The combination of capacitor 152 and inductor 48 tunes the receiver circuitry to the high frequency of the transmitter with the capacitor 152. The receiver is made sensitive to frequencies near the resonant frequency of the tuned circuit and less sensitive to frequencies away from the resonant frequency. A diode bridge 154 rectifies the alternating voltages. Capacitor 158 and resistor 164 filter out the high-frequency component of the receiver signal, and leaves the current pulse of the same duration as the bursts of the high-frequency signal. A zenor diode 169 is used for regulation and capacitor 166 blocks any net direct current.

Figure 18A:
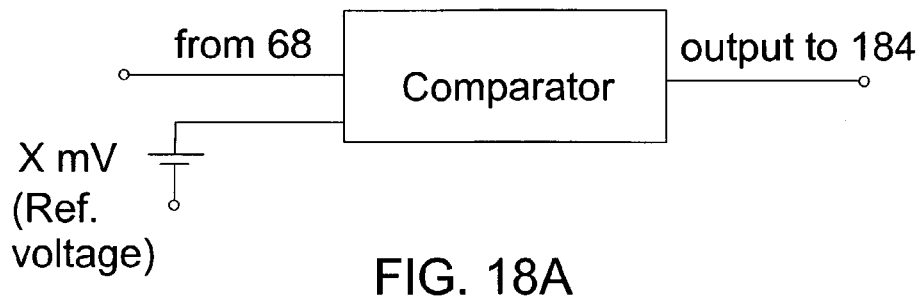
FIGS. 18A, 18B and 18C show output pulses from a comparater when input exceeds a reference voltage.
Figure 18B:
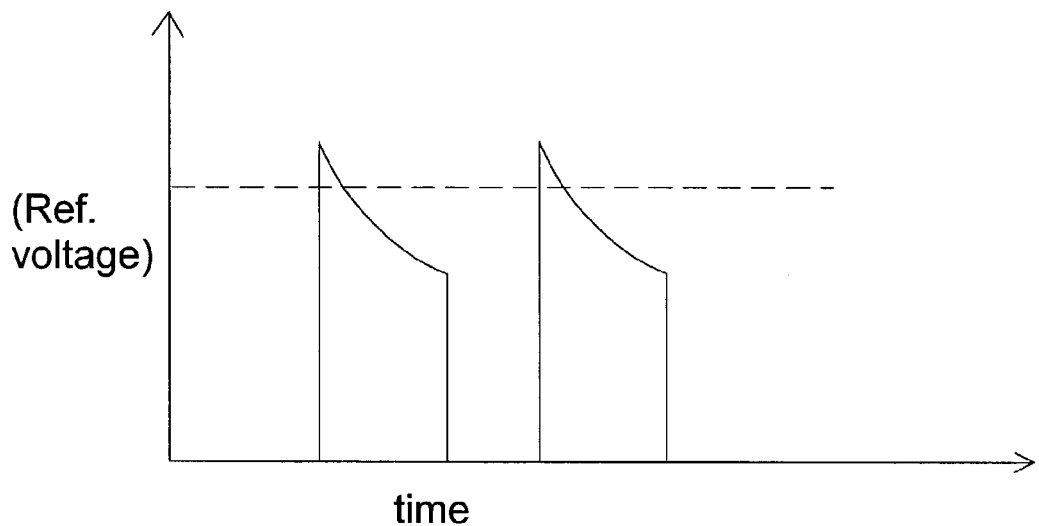
Figure 18C:
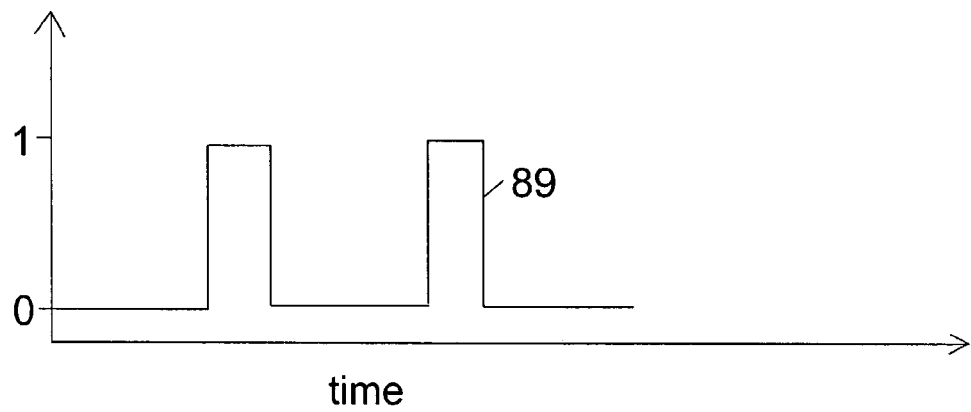

As shown in conjunction with FIG. 18A the pulses generated from the stimulus receive circuitry 68 are compared to a reference voltage, which is programmed in the stimulator. When the voltage of incoming pulses exceeds the reference voltage (FIG. 18B), the output of the comparator 178,180 sends a digital pulse 89 (shown in FIG. 18C) to the stimulation electric module 184. At this predetermined level, the high threshold comparator 178 fires and the controller 184 suspends any stimulation from the implanted pulse generator 70. The implanted pulse generator 70 goes into "sleep" mode for a predetermined period of time. In the presently preferred embodiment, the level of voltage needed for the battery operated stimulator to go into "sleep" mode is a programmable parameter. The length of time, the pulse generator 70 remains in "sleep" mode is also a programmable parameter. Therefore, advantageously the external stimulator in conjunction with the inductively coupled part of the stimulator 68 can be used as much as needed by the patient, and prescribed by the physician.

In the preferred embodiment, the external stimulator 42 is networked using the internet, giving the attending physician full control for activating and de-activating selected programs. Using "trial and error" various programs for electrical pulse therapy can be "titrated" for the individual patent. Also, by using the external stimulator 42, the battery 188 of the implanted stimulator unit 75 can be greatly extended. Further, even after the battery is depleted, the system can still be used for neuromodulation using the stimulus receiver module 68, and the external stimulator 42.

Figure 22:
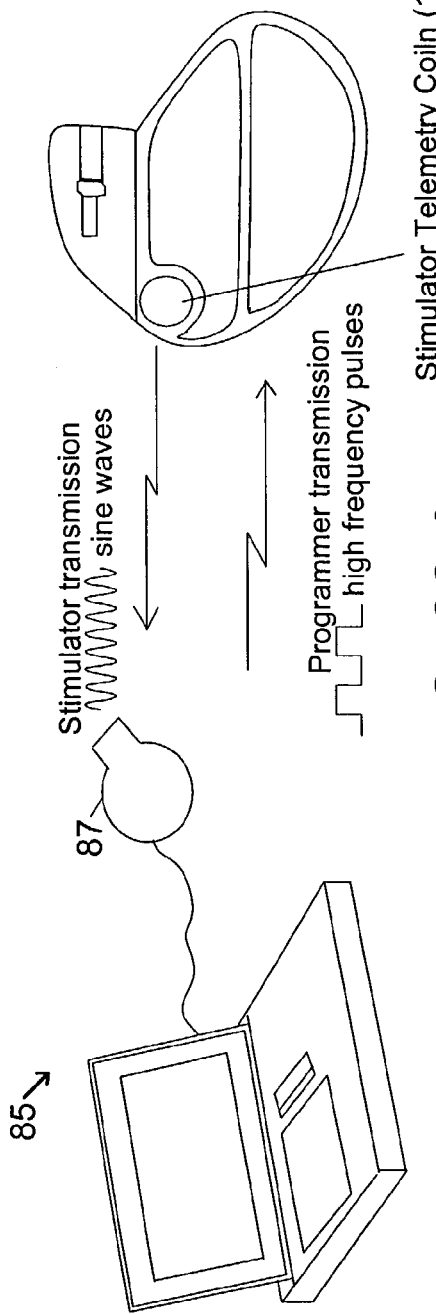
FIGS. 22A and 22B are diagrams showing communication of programmer with the implanted stimulator.
Figure 22:
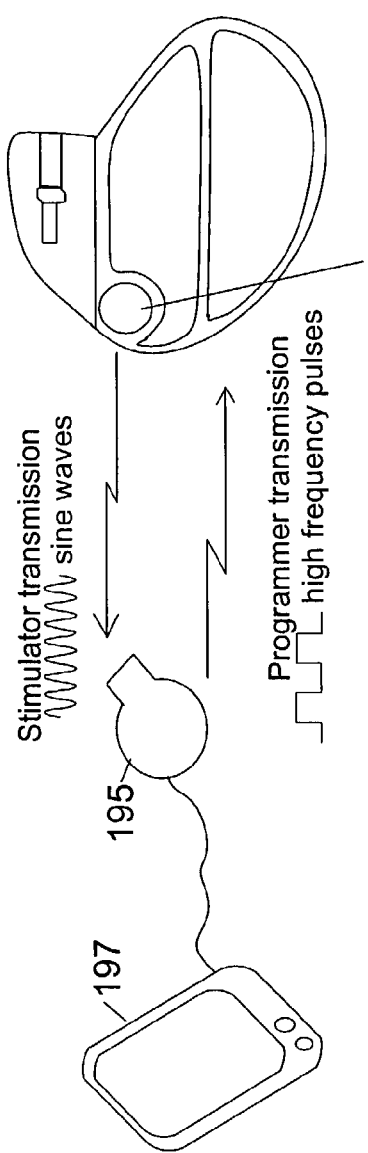

At some point, the implanted pulse generator 70 is programmed with the external programmer 85, using a modified PC and a programming wand 87, as is shown in FIGS. 22A and 22B.

Figure 17B:
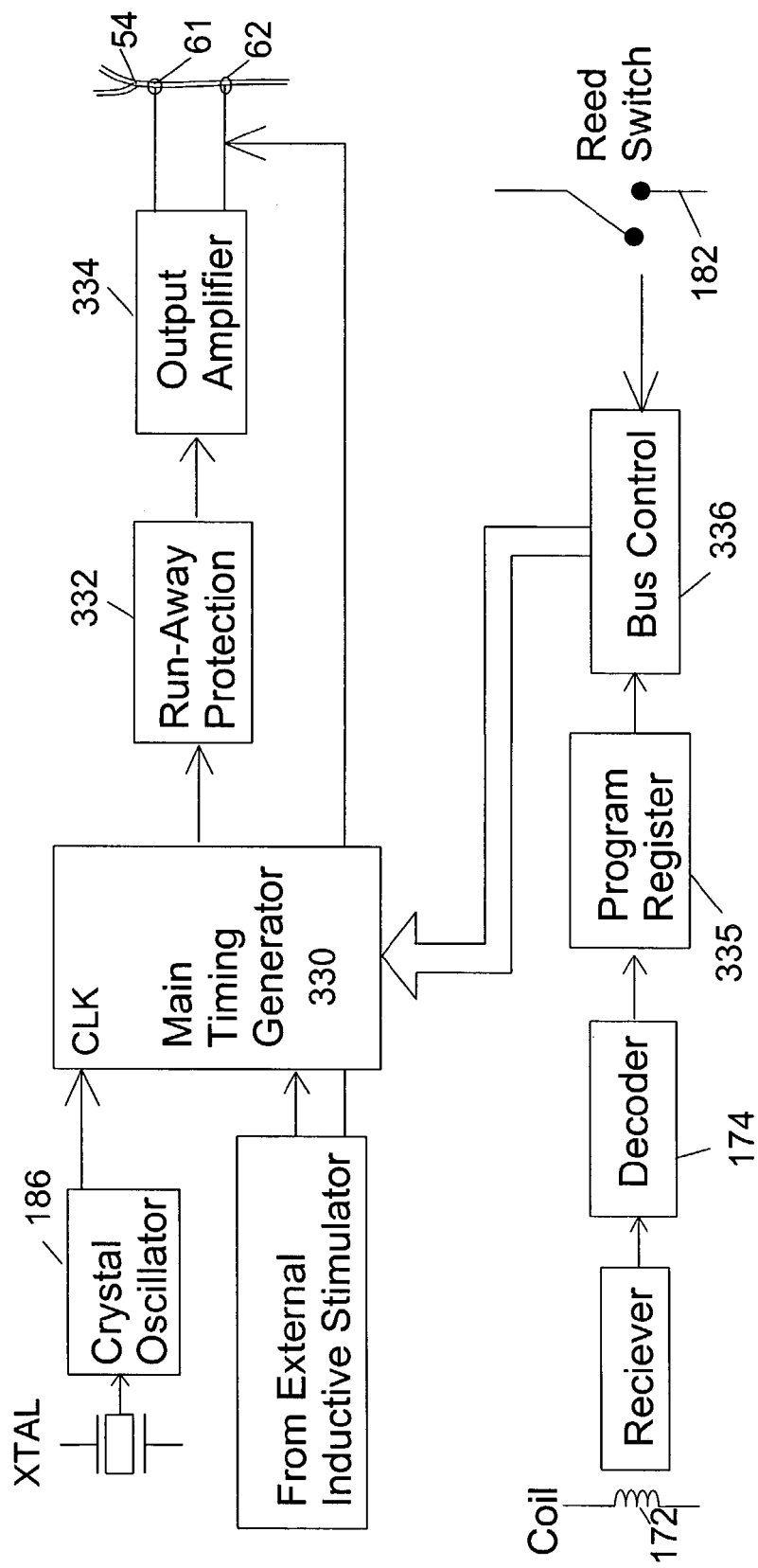
FIG. 17B shows details of implanted pulse generator.
Figure 17C:
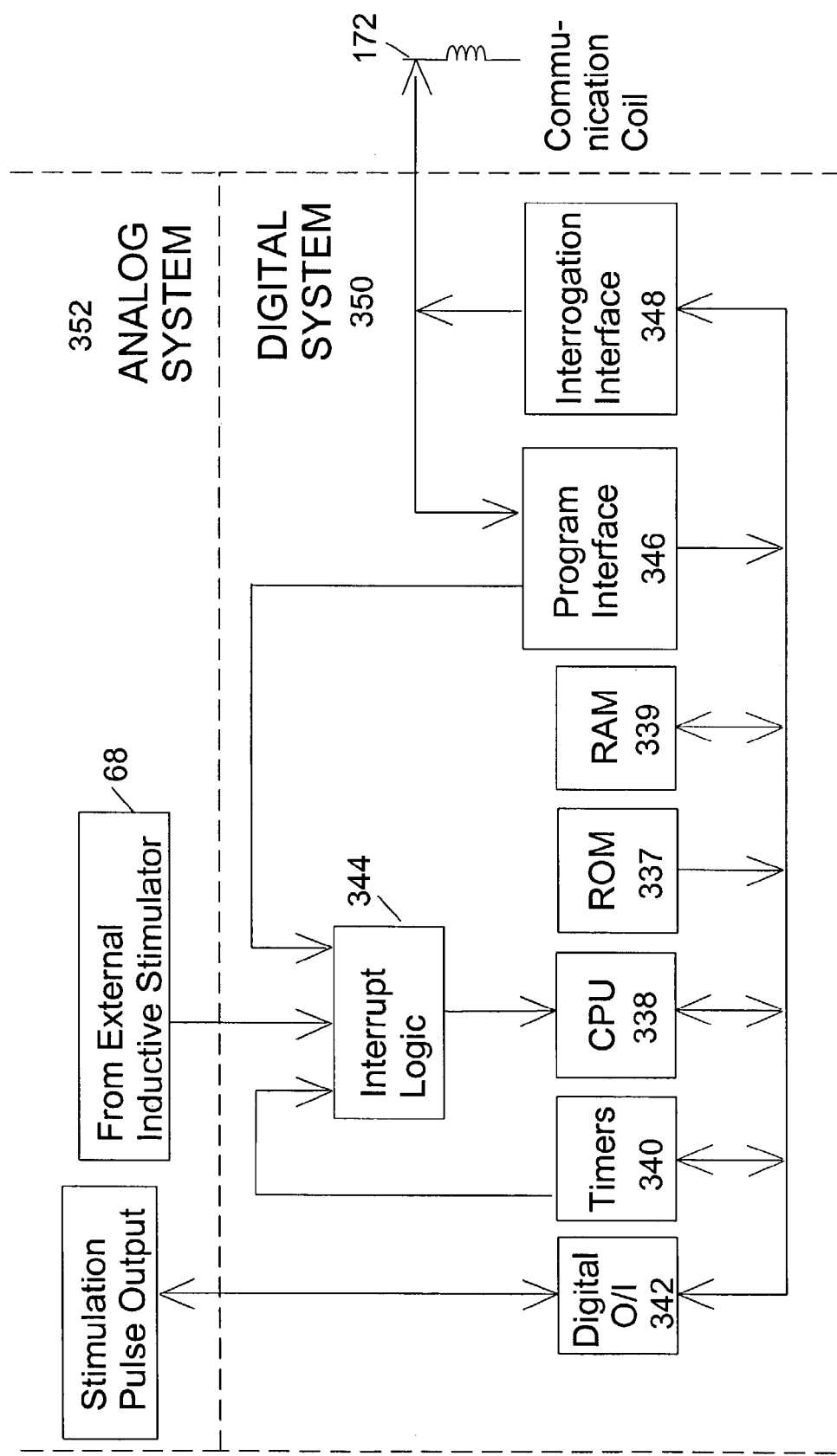
FIG. 17C shows details of implantable circuitry.

The battery operated portion of the system is shown on the right side of FIG. 17A and is described in conjunction with FIGS. 17B and 17C. The stimulation electronic module 184 comprises both digital and analog circuits. The main timing generator 330 (shown in FIG. 17B), controls the timing of the analog output circuitry for delivering neuromodulating pulses to the vagus nerve 54, via output amplifier 334. The main timing generator 330 receiving clock pulses from crystal oscillator 186. Main timing generator 330 also receiving input from inductively coupled circuitry 68 and programmer 85 via coil 172. FIG. 17C highlights other portions of the digital system such as CPU 338, ROM 337, RAM 339, Program interface 346, Interrogation interface 348, Timers 340, and Digital O/I 342.

FIG. 19A shows a picture of the implantable stimulator 75. FIG. 19B shows the pulse generator with some of the components used in assembly in an exploded view. These components include a coil cover 7, the secondary coil 48 and associated components, a magnetic shield 9, and a coil assembly carrier 11. The coil assembly carrier 11 has at least one positioning detail 80 located between the coil assembly and the feed through for positioning the electrical connection. The positioning detail 80 secures the electrical connection.

Figure 20A:
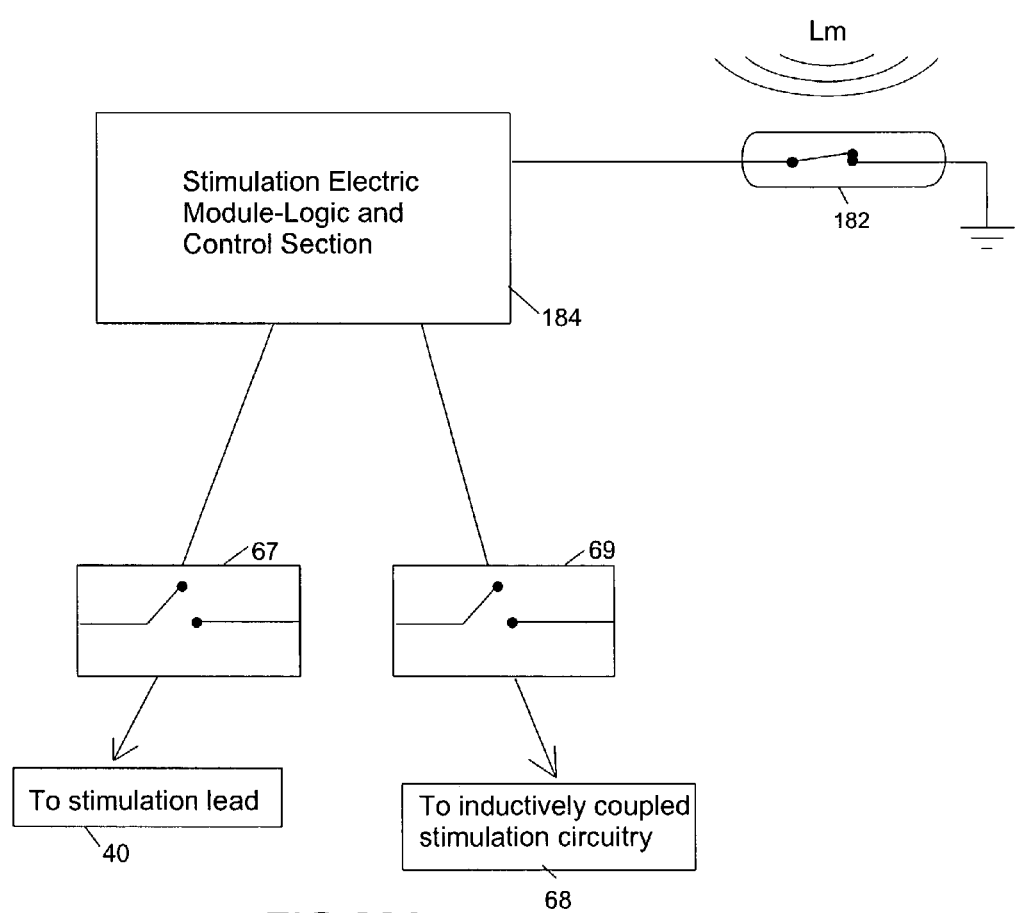
FIGS. 20A and 20B are simplified block diagrams showing the switching relationships between the inductively coupled and battery powered assemblies of the pulse generator.
Figure 20B:
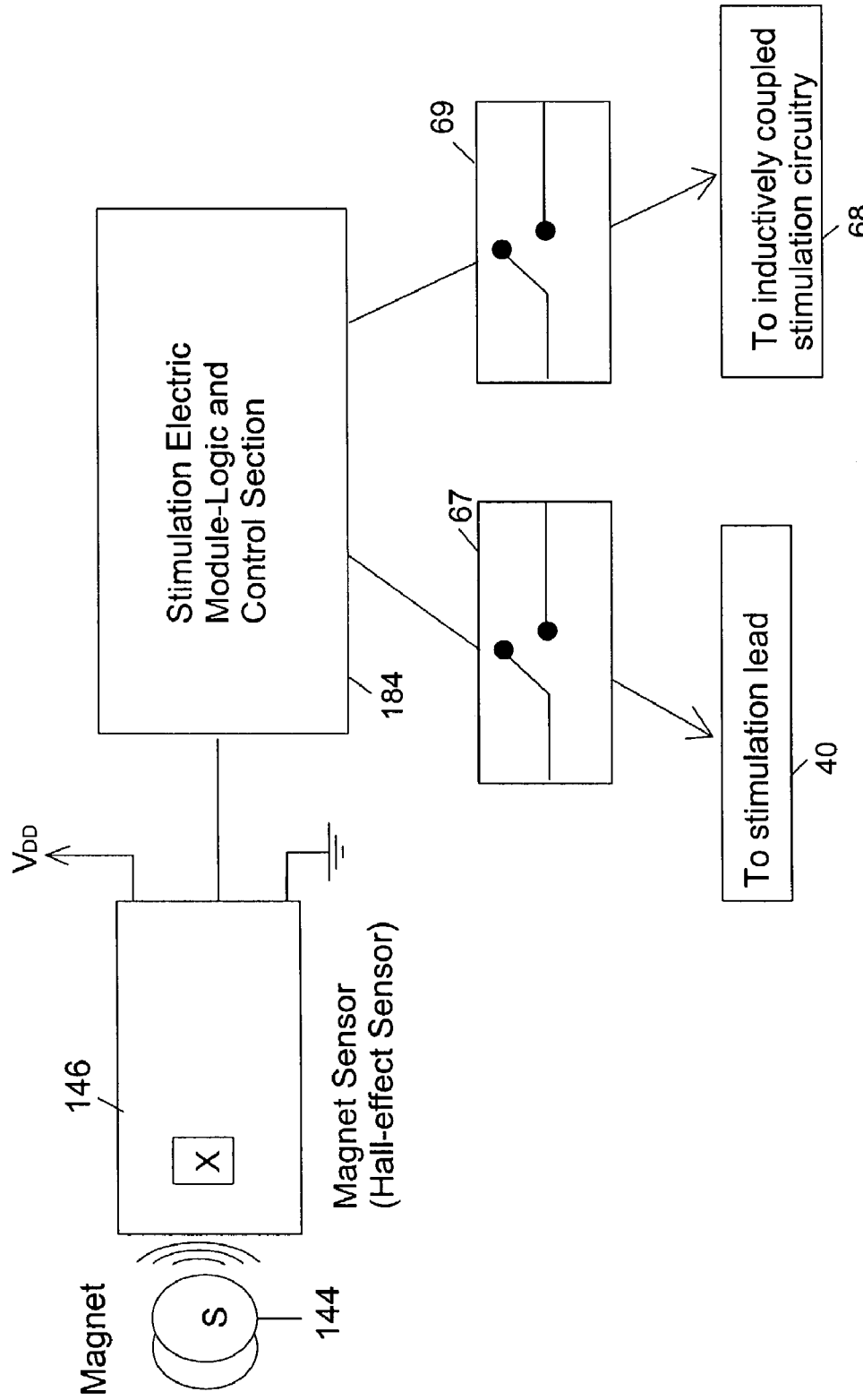
Figure 21:
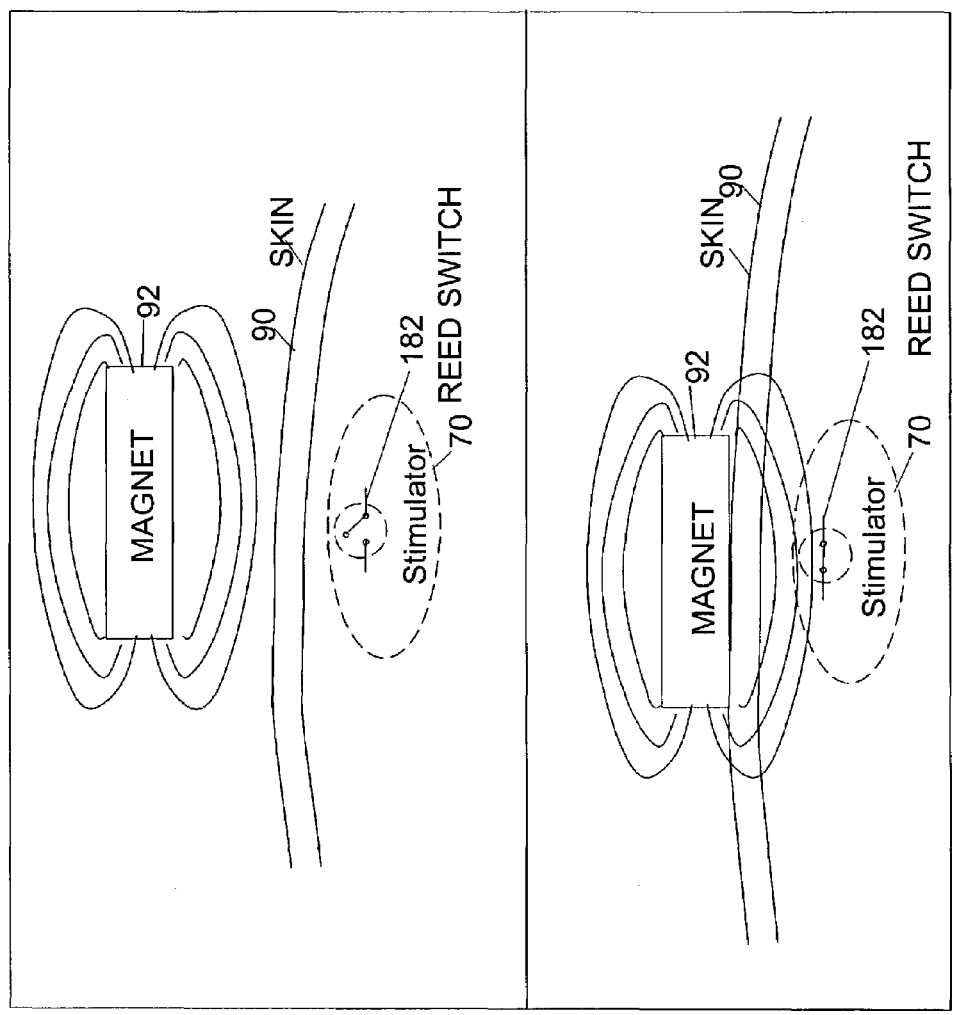
FIG. 21 is a diagram depicting the closure of a magnetic (Reed) switch with a magnet.

FIG. 20A is a simplified diagram of one aspect of control circuitry. In this embodiment, to program the implanted portion of the stimulator, a magnet is placed over the implanted pulse generator 70, causing a magnetically controlled Reed Switch 182 (which is normally in the open position) to be closed (shown in FIG. 21). As is also shown in FIG. 20A, at the same time a switch 67 going to the stimulator lead 40, and a switch 69 going to the circuit of the stimulus receiver module 68 are both opened, completely disconnecting both subassemblies electrically. Alternatively, as shown in FIG. 20B, instead of a reed switch 182, a solid state magnet sensor (Hall-effect sensor) 146 may be used for the same purpose. In the presently preferred embodiment, the solid state magnet sensor 146 is preferred, since there are no moving parts that can get stuck.

Figure 15:
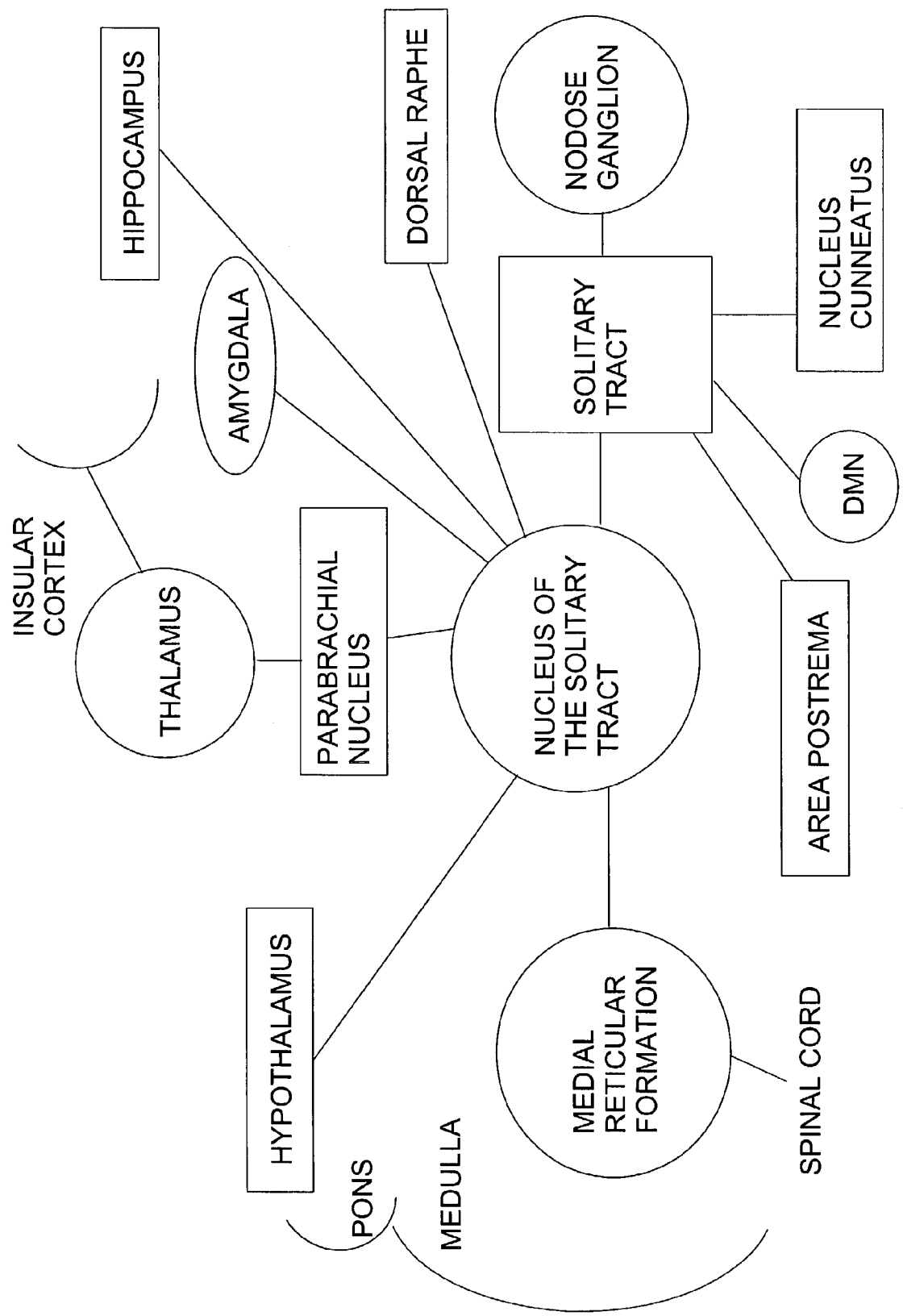
FIG. 15 is a block diagram illustrating the connections of solitary tract nucleus to other centers of the brain.
Figure 16:
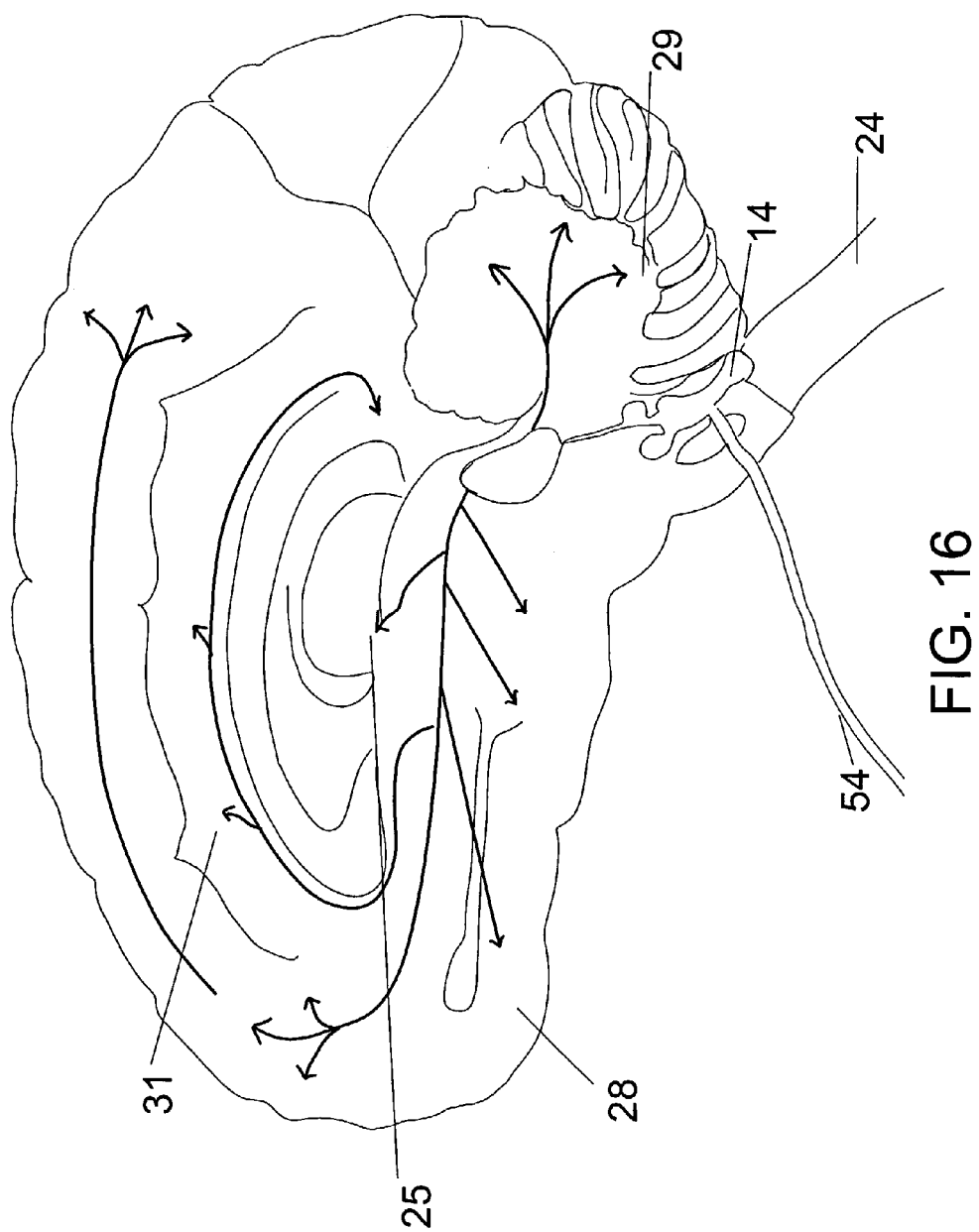
FIG. 16 is a schematic diagram of brain showing the relationship of the solitary tract nucleus to other centers of the brain.

With the magnet sensor switch 146 (or Reed Switch 182) in the closed position, a coil 192 in the head of the programmer, communicates with a telemetry coil 172 (shown in FIG. 15) of the implanted pulse generator 70. Bidirectional inductive telemetry is used to exchange data with the implanted unit 70 by means of the external programming unit 85. Inductive coupling is also employed to transmit the programming instructions, which are detected by a receiving element, which is the antenna coil 172. These pulses of the magnetic field are transmitted in a coding scheme that induces current to flow in the antenna coil 172. Programming takes place via a coil 172, a receiving amplifier, a decoder, a controller, and the register in which the temporary and permanent programs are stored. Radiofrequency (RF) waves of the electromagnetic field using frequencies of approximately 100 KHz, that allow rapid transmission of large amounts of information. Both the transmitter (in the programmer) and the receiver (in the pulse generator 172) have antennae (coils) for emitting and decoding RF signals. The RF frequency is modulated, allowing the encoding of information during transmission by the programmer 85. The receiver coil 172 is tuned through properly selected inductor-capacitor values to have unique sensitivity to the carrier frequency of the transmitted signals.

The transmission of programming information involves manipulation of the carrier signal in a manner that is recognizable by the pulse generator as a valid set of instructions (shown in conjunction with FIGS. 22A and 22B). The process of modulation serves as a means of encoding the programming instruction in a language that is interpretable by the pulse generator. Modulation of signal amplitude, pulse width, and time between pulses are all used in the programming system, as will be appreciated by those skilled in the art. FIG. 23A shows an example of pulse count modulation, and FIG. 23B shows an example of pulse width modulation.

Figure 24:
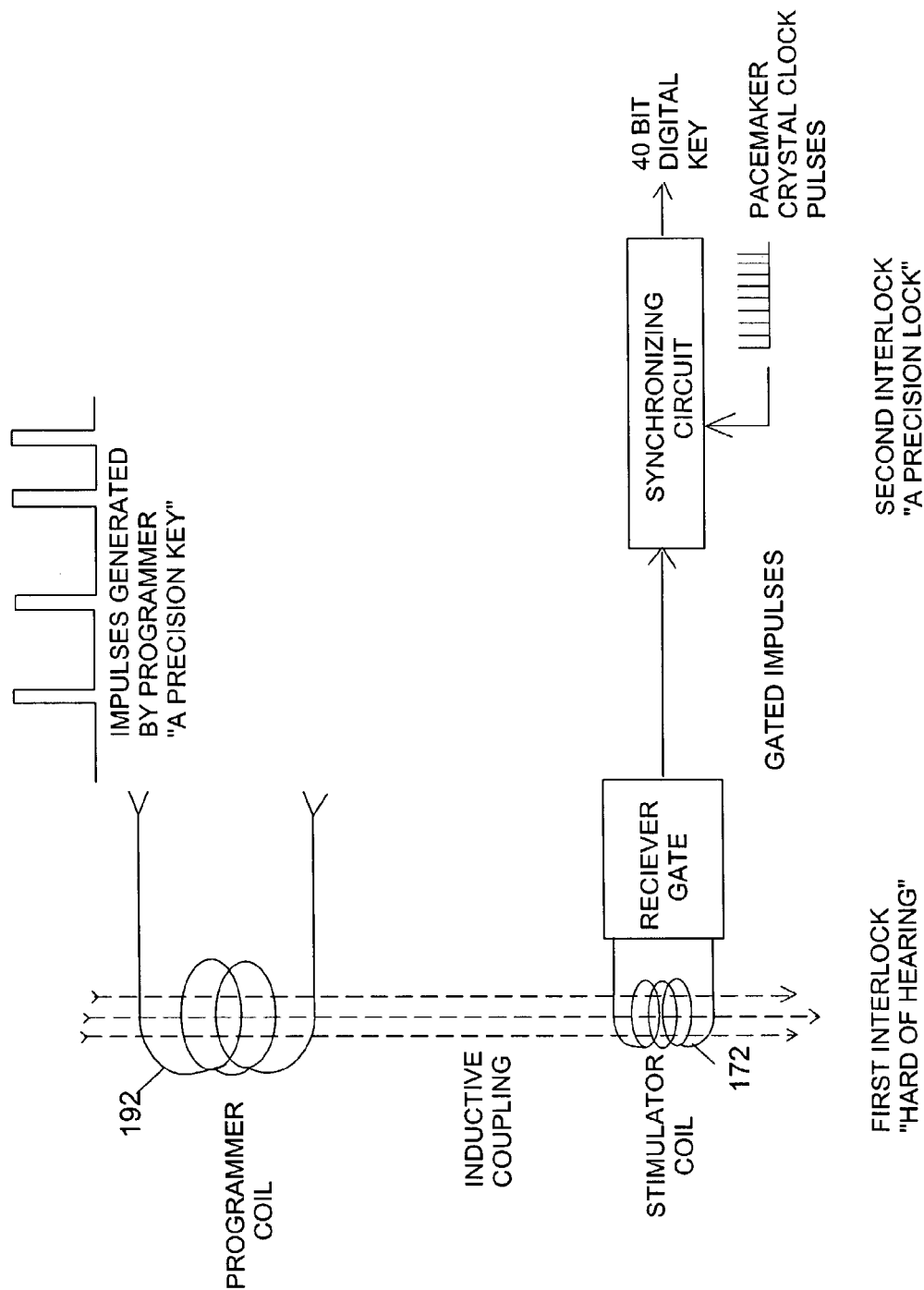
FIG. 24 diagrammatically represents secure communication for programming pulses.

The programming signal of the current system is designed to be secure. Several schemes can be used, as will be appreciated by those skilled in the art. For example, using the first group of bits and pulses as an identification or access code. Another example of programming signal security is shown in FIG. 24. An x number of pulses are organized into pairs to send a code message of x/2 digital bits that allow different levels of "safety interlocks".

Figure 25:
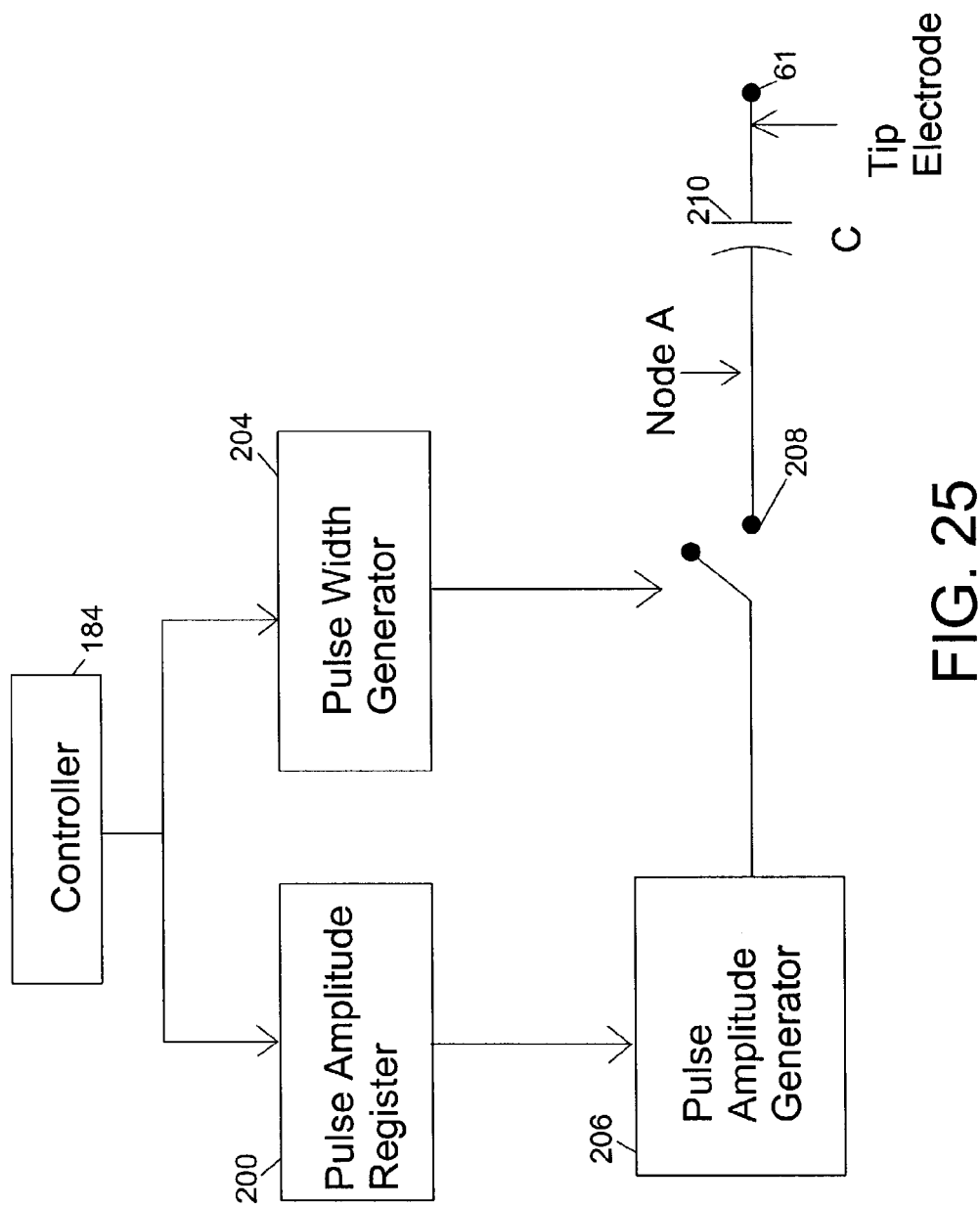
FIG. 25 is a block diagram for generation of a pre-determined stimulation pulse.

Once the implanted pulse generator 70 is programmed, it operates continuously until a signal is received from the stimulus receiver module 68, via the high threshold comparator 178. As shown in FIG. 17A, the controller 184 of the subassembly 70 controls the output amplifiers. The pulses have predetermined energy (pulse amplitude and pulse width) and are delivered at a time determined by the therapy stimulus controller. The circuitry in the output amplifier, shown in conjunction with (FIG. 25) generates an analog voltage or current that represents the pulse amplitude. The stimulation controller module 184 initiates a stimulus pulse by closing a switch 208 that transmits the analog voltage or current pulse to the nerve tissue through the tip electrode 61 of the lead 40. The output circuit receiving instructions from the stimulus therapy controller 184 that regulates the timing of stimulus pulses and the amplitude and duration (pulse width) of the stimulus. The pulse amplitude generator 206 determines the configuration of charging and output capacitors necessary to generate the programmed stimulus amplitude. The output switch 208 is closed for a period of time that is controlled by the pulse width generator 204. When the output switch 208 is closed, a stimulus is delivered to the tip electrode 61 of the lead 40.

Figure 26:
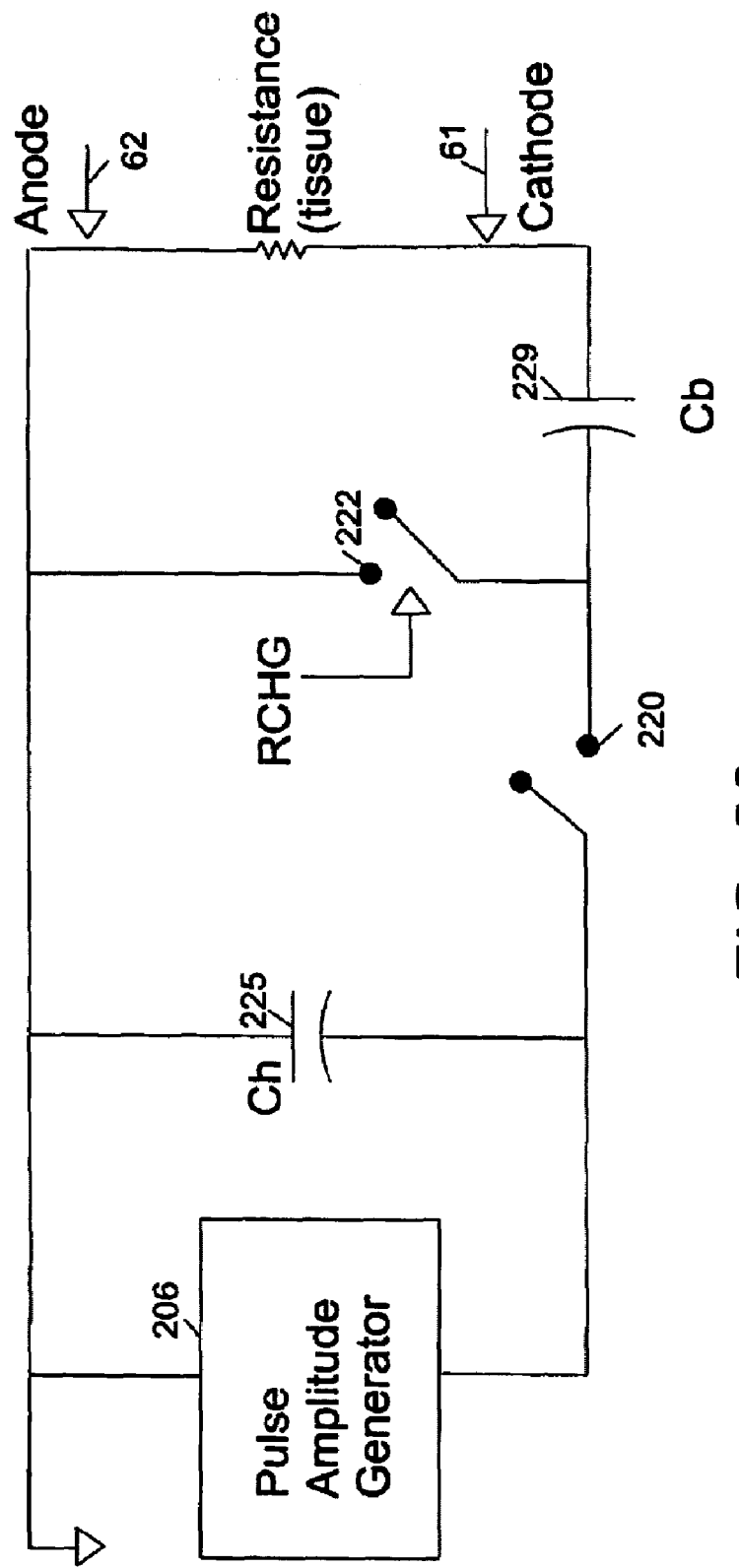
FIG. 26 is a schematic for delivering stimulation pulses.

The constant-voltage output amplifier applies a voltage pulse to the distal electrode (cathode) 61 of the lead 40. A typical circuit diagram of a voltage output circuit is shown in FIG. 26. This configuration contains a stimulus amplitude generator 206 for generating an analog voltage. The analog voltage represents the stimulus amplitude and is stored on a holding capacitor $C_h$ 225. Two switches are used to deliver the stimulus pulses to the lead 40, a stimulating delivery switch 220, and a recharge switch 222, that reestablishes the charge equilibrium after the stimulating pulse has been delivered to the nerve tissue. Since these switches have leakage currents that can cause direct current (DC) to flow into the lead system 40, a DC blocking capacitor $C_b$ 229, is included. This is to prevent any possible corrosion that may result from the leakage of current in the lead 40. When the stimulus delivery switch 220 is closed, the pulse amplitude analog voltage stored in the ($C_h$ 225) holding capacitor is transferred to the cathode electrode 61 of the lead 40 through the coupling capacitor, $C_b$ 229. At the end of the stimulus pulse, the stimulus delivery switch 220 opens. The pulse duration being the interval from the closing of the switch 220 to its reopening. During the stimulus delivery, some of the charge stored on $C_h$ 225 has been transferred to $C_b$ 229, and some has been delivered to the lead system 40 to stimulate the nerve tissue.

To re-establish equilibrium, the recharge switch 222 is closed, and a rapid recharge pulse is delivered. This is intended to remove any residual charge remaining on the coupling capacitor $C_b$ 229, and the stimulus electrodes on the lead (polarization). Thus, the stimulus is delivered as the result of closing and opening of the stimulus delivery 220 switch and the closing and opening of the RCHG switch 222. At this point, the charge on the holding $C_h$ 225 must be replenished by the stimulus amplitude generator 206 before another stimulus pulse can be delivered.

Referring back to FIG. 17A, for the implanted power source, lithium iodine is preferred in the current embodiment, because of its long history in cardiac pacemakers. However, other power sources where lithium is combined with other cathode materials may be used, such as lithium cooper sulfide, lithium silver vanadium pentoxide, lithium bromine chloride, or lithium sulfuryl chloride cell.

Figure 27:
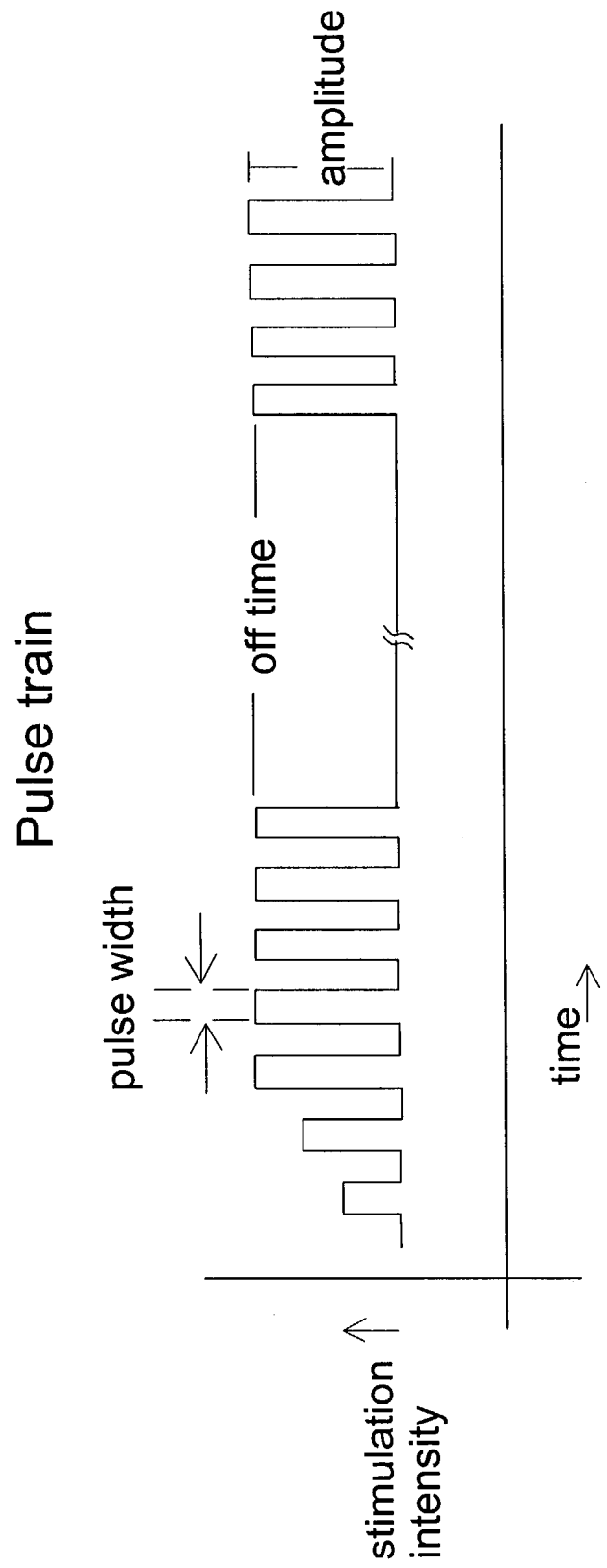
FIG. 27 is a diagram depicting ramping-up of a pulse train.

FIG. 27 shows an example of the pulse trains that are delivered. The microcontroller is configured to deliver the pulse train as shown in the figure, i.e. there is ramping up of the pulse train. The purpose of the ramping-up is to avoid sudden changes in stimulation, when the pulse train begins.

Figure 28:
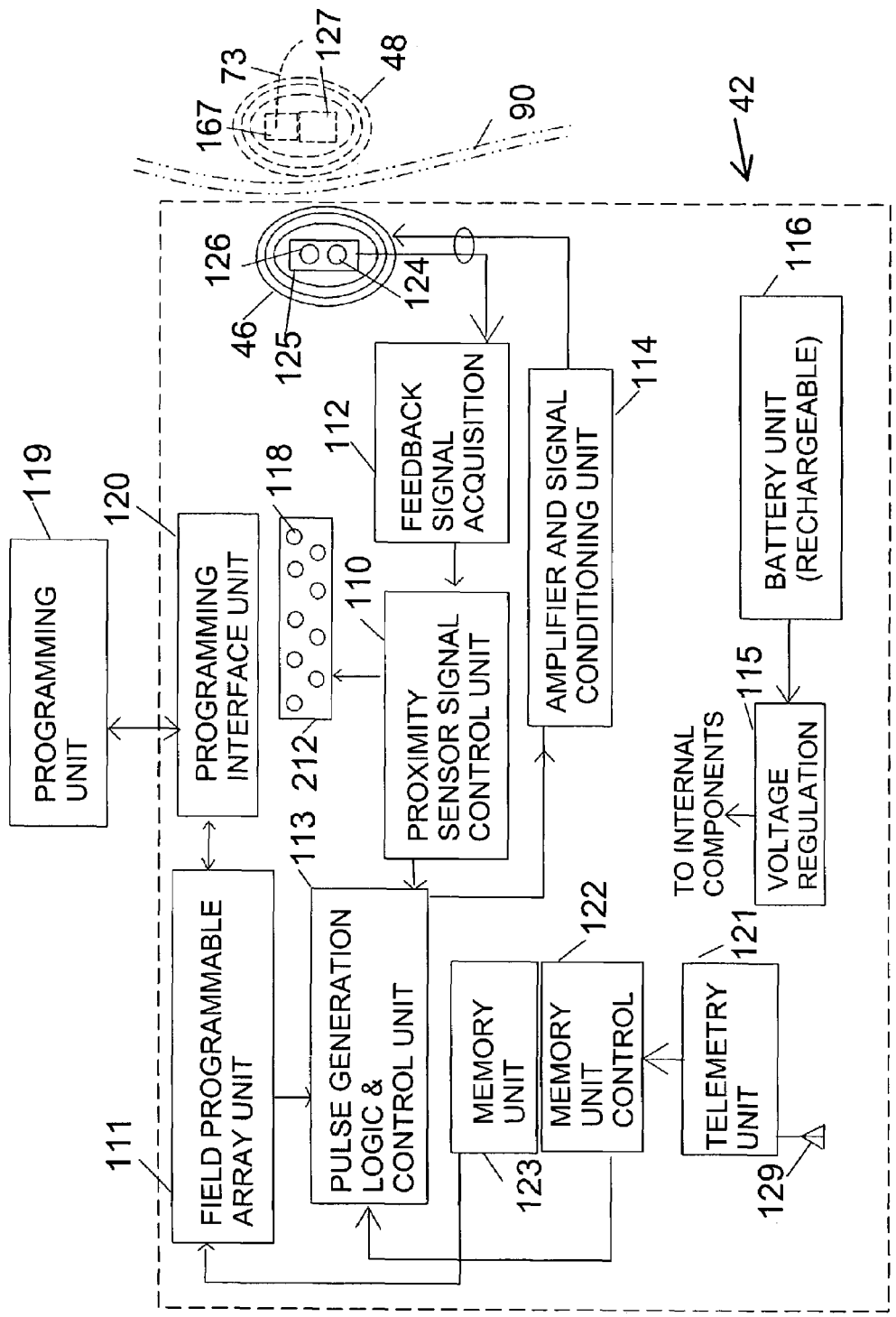
FIG. 28 is a functional block diagram of the external stimulator.

As shown in FIG. 28, the external pulse generator 42 is composed of three modules or sub-assemblies. The first sub-assembly is the pulse generation and signal conditioning components 113,114, the second is the battery 116, and the third is the telemetry and memory unit 121. The presently preferred embodiment, comprises proximity sensing and feedback circuitry, even though the pulse generator is able to function as supplier of electric pulses to the nerve tissue without the proximity feedback loop and the telemetry module. These modules or sub-assemblies also provide for a scalable external pulse generator 42. In the telemetry module, a wireless antenna 129 provides a means of communication to the external pulse generator 42 and the wireless remote server 189. A programming unit 119 can be physically connected to the stimulator 42 (via the Programming Unit Interface 120) in a tethered manner for loading of new predetermined programs or changing parameters of an existing program.

Also shown in conjunction with FIG. 28, the pre-packaged programs are stored in the memory unit 123. This represents memory with a readable and writeable portion and a non-volatile pre-programmable portion. A Field Programmable Array Unit (FPGA) 111 and a random access component (RAM) and Random addressable storage logic, facilitates the application of logic to edit and change the "current" parameters being utilized for pulse generation. The programmable unit interface 120 provides an interface to a programming unit (portable computer system) 119, which allows re-loading of a new set of predetermined programs. The pulse generation component 113 generates pulses of well-defined parameters, selected from the programmed parameters that exist in the memory unit 123. The pulse signal generation unit 113 provides its signal to be amplified and conditioned at the amplifier and signal conditioning unit 114 which then provides these signals to the primary (external) inductive coil 46. In one embodiment, the sensor unit 126 has a pair of sensors which sense the position of the implanted magnet 127, and the sensor signal is fed back to the proximity sensor control block 110 via the feedback signal conditioning unit 112. The feedback signal provides a proportional signal for modification of the frequency, amplitude and pulse-width of the pulse being generated by the pulse signal generator unit 113. The sensor unit 126 has two sensors 124, 125 that sense the location of the implanted magnet 127. The implanted (secondary) coil 48 is rigidly connected to the passive circuit and magnet 127. The skin 90 separates the subcutaneous and external components. The external components are placed on the skin, with the primary coil 46 in close proximity and optimally situated with respect to the implanted (secondary) coil 48.

Figure 29:
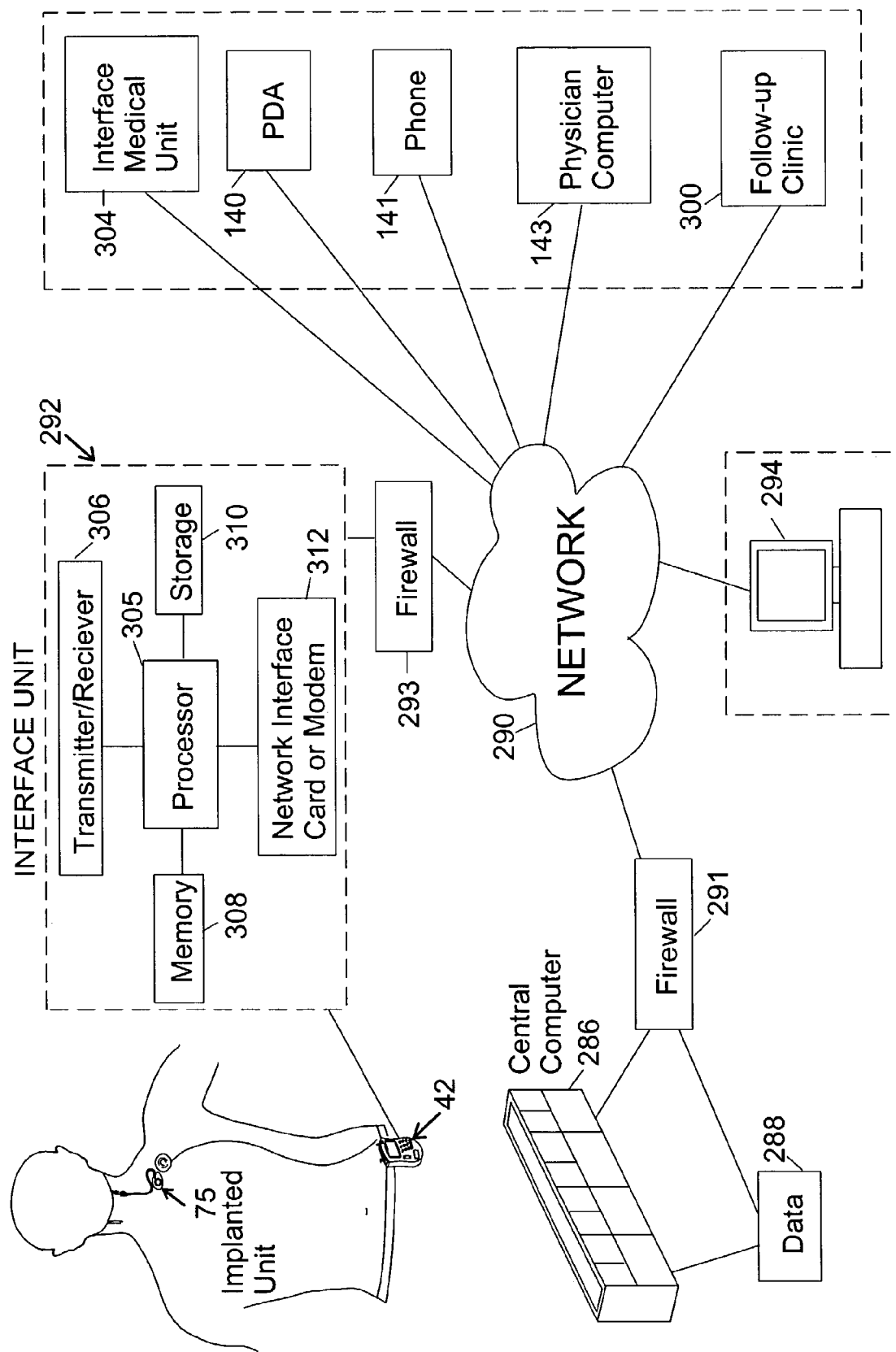
FIG. 29 is a block diagram of the networking interface board.

As shown in FIG. 29, in one aspect of the invention the external stimulator 42 and the programmer 85 are capable of being networked 290 to a central collaboration computer 286 as well as other devices such as a remote computer 294, PDA 140, phone 141, physician computer 143. This also minimizes situations in which the physical transport of a patient to a particular clinical setting is required. The implanted unit 75 communicates with the external stimulator 42 via inductive coupling between primary 46 and secondary coil 48.

The interface unit 292 in the preferred embodiment communicates with the central collaborative network 290 via land-lines such as cable modem or wirelessly via the internet. A central computer 286 which has sufficient computing power and storage capability to collect and process large amounts of data, contains information regarding device history and serial number, and is in communication with the network 290. Communication over collaboration network 290 may be effected by way of a TCP/IP connection, particularly one using the internet, as well as a PSTN, DSL, cable modem, LAN, WAN or a direct dial-up connection.

The standard components of interface unit shown in block 292 are processor 305, storage 310, memory 308, transmitter/receiver 306, and a communication device such as network interface card or modem 312. In the preferred embodiment these components are embedded in the external stimulator 42 and can alternatively be embedded in the programmer 85. These can be connected to the network 290 through appropriate security measures 293.

Another type of remote unit that may be accessed via central collaborative network 290 is remote computer 294. This remote computer 294 may be used by an appropriate attending physician to instruct or interact with interface unit 292, for example, instructing interface unit 292 to send instruction downloaded from central computer 286 to remote implanted unit 75.

Figure 30:
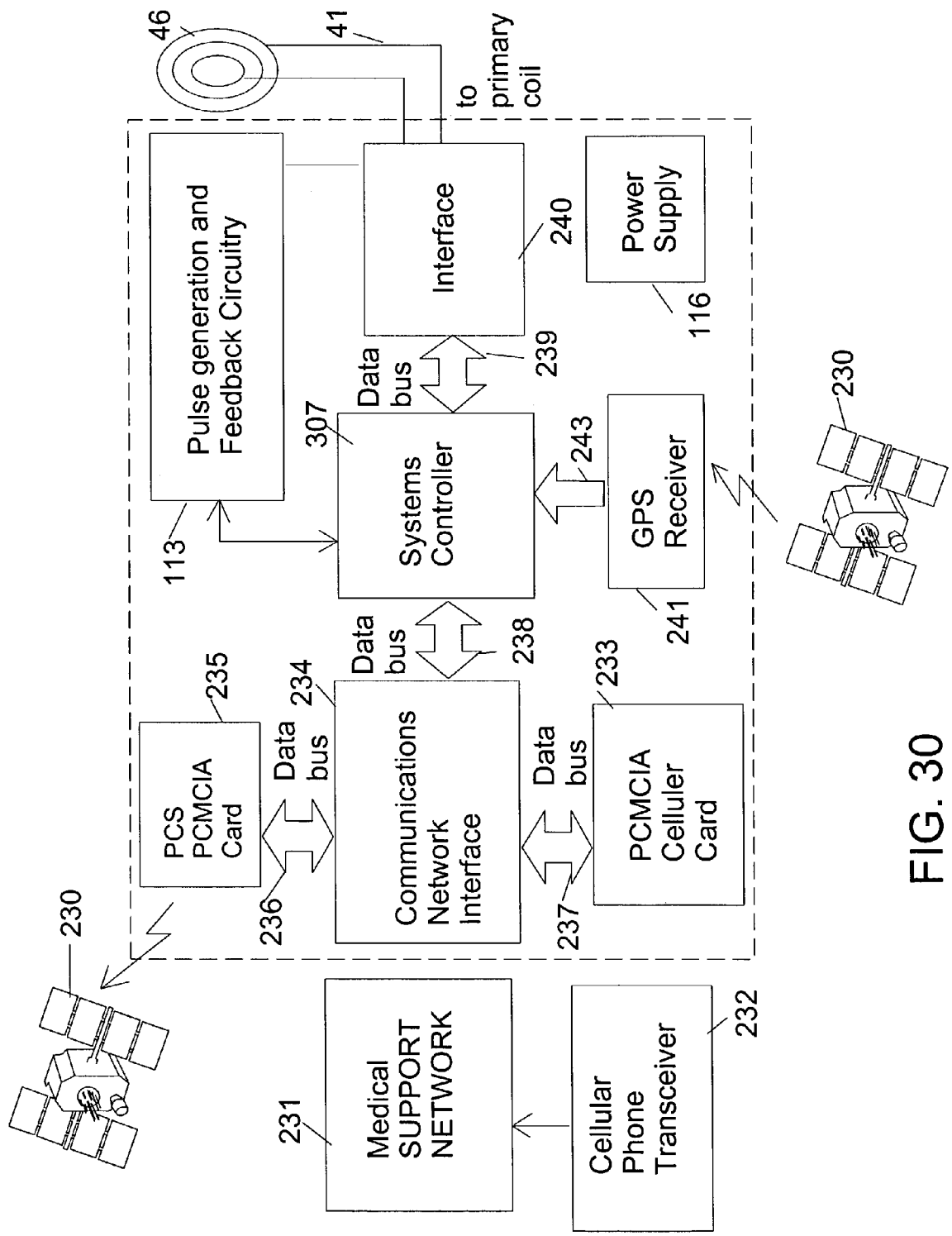
FIG. 30 is block diagram of the location tracking interface board.

In one embodiment of the system, as shown in conjunction with FIG. 30, the programmer 85 also comprises GPS receiver 241 for location tracking. Alternatively, the location tracking circuitry may be incorporated in the external stimulator 42. The system controller 307 contains a system lock for maintaining an accurate time base which may be recalibrated periodically via accurate clocks in the GPS satellites 230. The microcomputer-based systems controller 307 is coupled to data communications network interface via data bus 238. The system controller 307 may be part of a standard or modified cellular telephone or other personnel communication device.

At a medical support network 231, a base station is provided to be in the communication link with the patient-worn communication device. The base station is preferably a microprocessor-based system that includes the software and hardware needed for communication with the patients to locate the patient.

In accordance with one aspect of the invention, the system controller 307 is coupled to a GPS receiver 241 via bus 243 for receiving patient positioning data from an earth satellite 230. The GPS receiver 241 may use current systems such as the PCMCIA GPS Sensor. The GPS receiver 241 may be actuated by a command received through the system controller 307 from the medical support network 231 in the case of an emergency response.

Either or both PCMCIA cards 235 and 233 may be provided and they are coupled with the voice and communications network 234 via buses 236 and 237. When both are provided access to the communications satellite link 230 is automatically obtained when a link to a cellular transceiver 232 is not possible.

Figure 31:
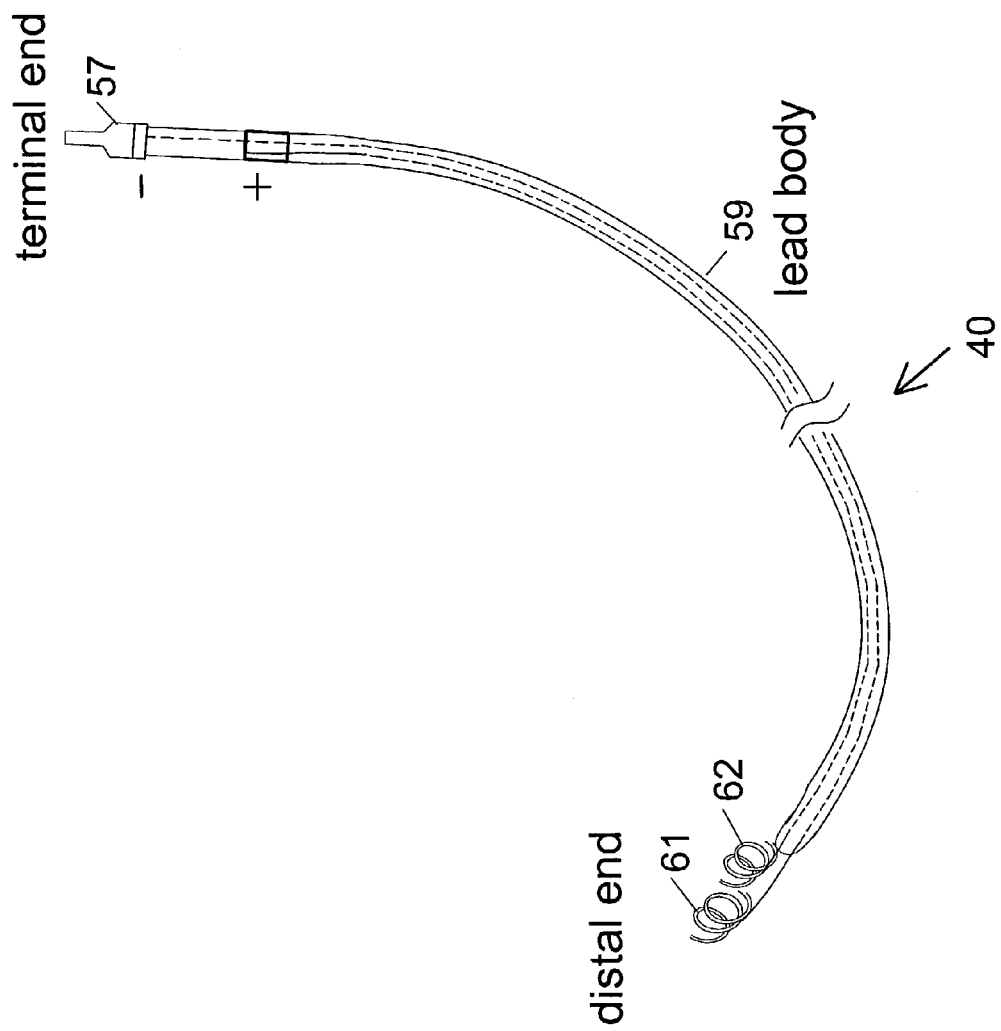
FIG. 31 is a diagram of an implantable lead.

Moving now to FIG. 31, the implanted lead 40 component of the system is similar to cardiac pacemaker leads, except for distal portion of the lead. In the presently preferred embodiment, the lead terminal is a linear bipolar (though a bifurcated terminal can also be used), and plug(s) into the cavity of the pulse generator 75. The lead body insulation 59 may be constructed of polyurethane, medical grade silicone, or silicone reinforced with polytetrafluoro-ethylene (PTFE). The electrodes for stimulating the vagus nerve may either wrap around the nerve once or may be spiral shaped. These stimulating electrodes may be made of pure platinum, platinum/Iridium alloy or platinum/iridium coated with titanium nitride, and are described more fully in U.S. Pat. No. 6,205,359 and incorporated here by reference. The conductor connecting the terminal to the electrodes is made of an alloy of nickel-cobalt.

The choices for implanted lead design variables are also summarized in the table below.

Table of lead design variables

| Proximal End | | | | | Distal End |
|---|---|---|---|---|---|
| Lead Terminal | Lead body-Insulation Materials | Lead-Coating | Conductor (connecting proximal and distal ends | Electrode - Material | Electrode - Type |
| Linear Bipolar | Polyurethane | Antimicrobial coating | Alloy of Nickel-Cobalt | Pure Platinum | Spiral electrode |
| Bifurcated | Silicone | Anti-Inflamatory coating | | Platinum-Iridium (Pt/IR) Alloy | Wrap-around electrode |
| | Silicone with Polytetrafluoro-ethylene (PTFE) | Lubricious coating | | Pt/Ir coated with Titanium Nitride | Steroid eluting |
| | | | | Carbon | |

Once the lead 40 is fabricated, coating such as anti-microbial, anti-inflammatory, or lubricious coating may be applied to the body of the lead.

FIG. 32A summarizes an electrode-tissue interface. There is a thin layer of fibrotic tissue between the stimulating electrode 61 and the excitable nerve fibers of the vagus nerve 54. FIG. 32B summarizes the most important properties of the metal/tissue phase boundary in an equivalent circuit diagram. Both the membrane of the nerve fibers and the electrode surface are represented by parallel capacitance and resistance. Application of a constant battery voltage $V_{bat}$ from the pulse generator 75, produces voltage changes and current flow, the time course of which is crucially determined by the capacitive components in the equivalent circuit diagram. During the pulse, the capacitors $C_o$, $C_h$ and $C_m$ are charged through the ohmic resistances, and when the voltage $V_{bat}$ is turned off, the capacitors discharge with current flow on the opposite direction.

Figure 33:
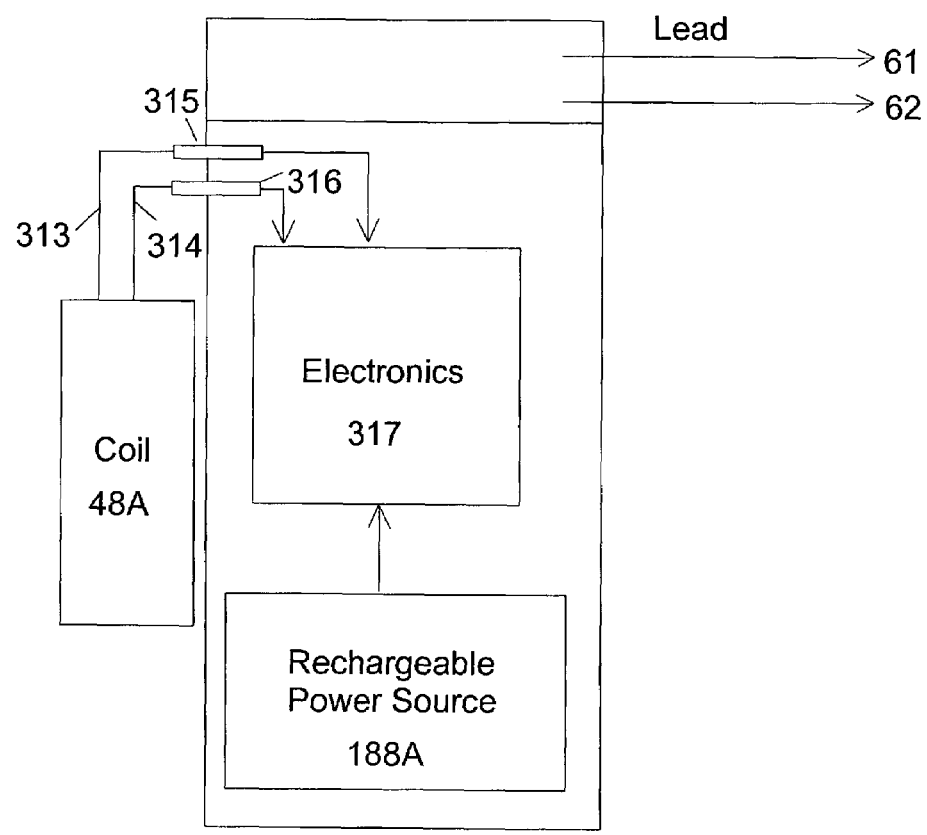
FIG. 33 depicts an embodiment where the system is used as an implantable, rechargeable system.

One of ordinary skill in the art will appreciate that with some modification in the circuitry the same concept can be adapted for an implantable, rechargeable power source. In such an embodiment (shown in conjuction with FIG. 33), the RF pulses transmitted via coil 46 and received via subcutaneous coil 48A are rectified via diode bridge 154. These DC pulses are processed and the resulting current applied to recharge the battery 188A in the implanted pulse generator.

Figure 34:
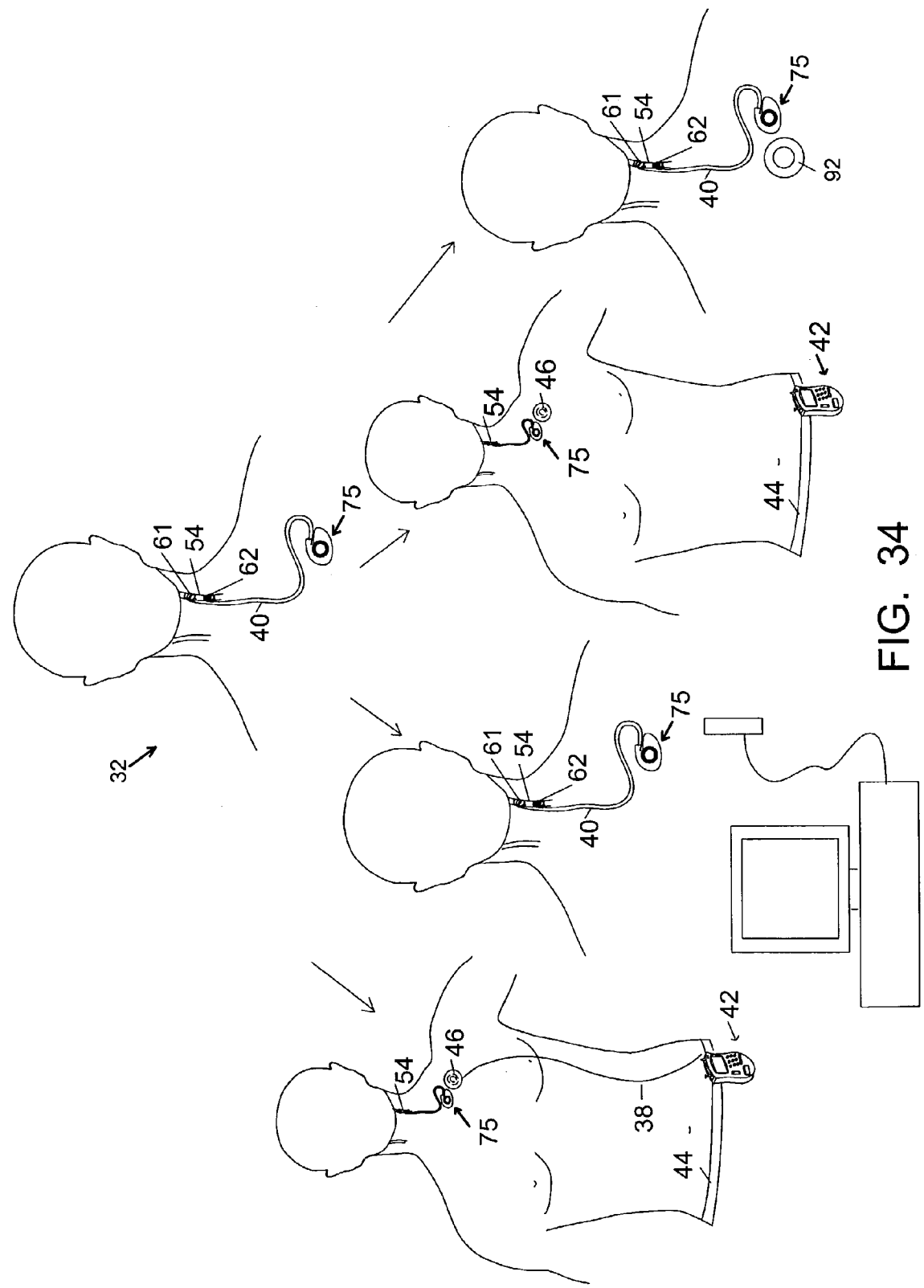
FIG. 34 is a diagram depicting different varieties of the system of the invention.

It will also be obvious to one of ordinary skill in the art that, the current invention can be practiced with a cheaper and less programmable version of an implantable pulse generator. For example, as shown in FIG. 34 (bottom right), a programmer-less stimulator may be used, where a limited number of programs may be accessed via a magnet, preferably as disclosed in U.S. Pat. No. 6,449,512 and incorporated here by reference.

Figure 35:
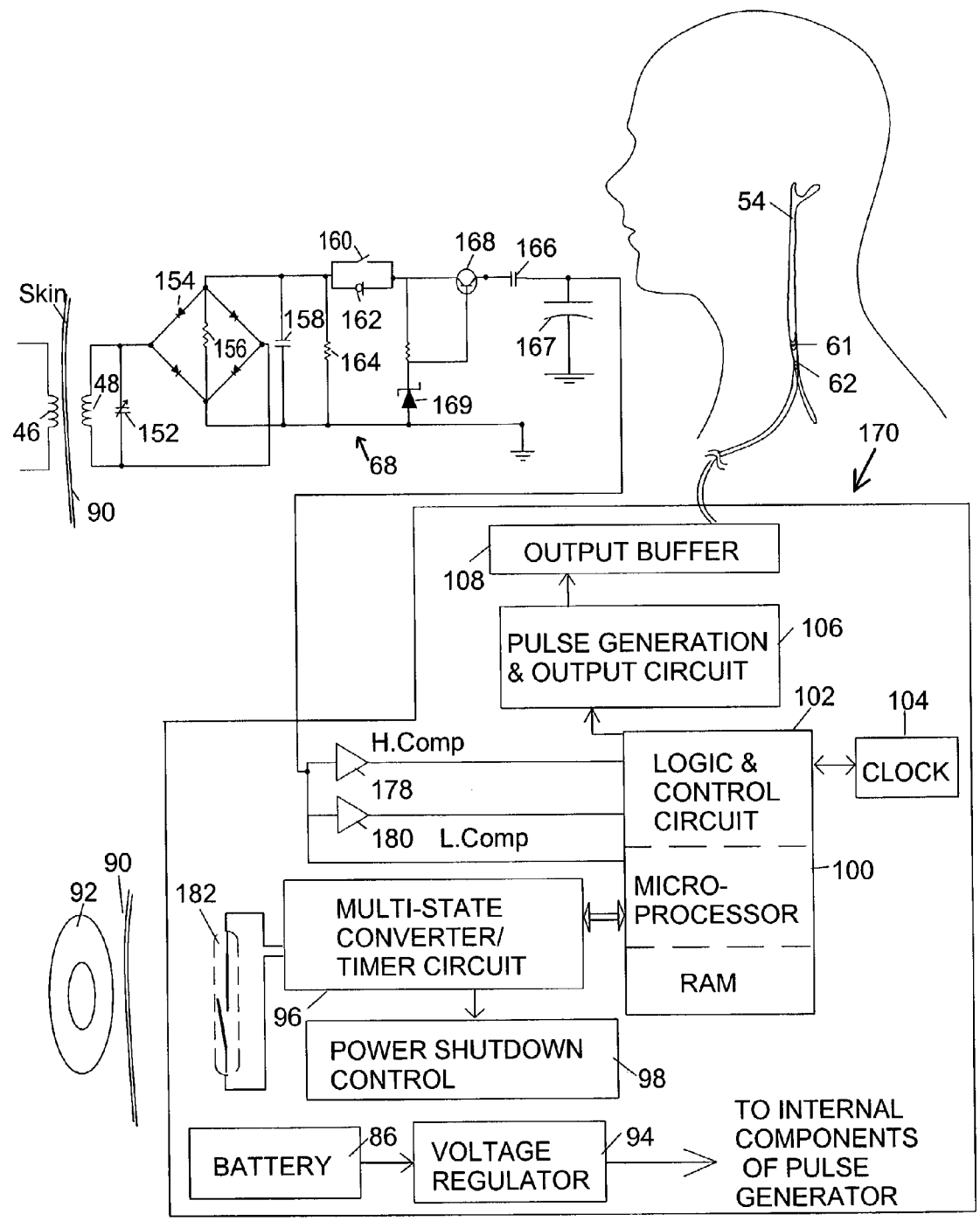
FIG. 35 is a schematic and block diagram depicting a simpler version of the pulse generator.

As shown with reference to FIG. 35, in this version only a limited number of states are possible. For example LO, MED, MED-HI, HI stimulation states and an OFF state. Each state corresponds to a complete program comprising a unique combination of pulse amplitude, pulse width, pulses per second, ON-time and OFF-time. By using just a magnet 92, each of these states can be programmed by swiping the magnet 92, different number of times. For example, once, twice, three times etc. Once the pulse generator 170 is programmed to a particular state, it supplies stimulation pulses to the vagus nerve 54 according to the programmed state, until stimulation energy is received from the inductively coupled part of the system 68. When energy is received from inductively coupled part of the system 68, the battery operated portion goes into "sleep mode" for a predetermined period of time which is programmed.

Figure 36:
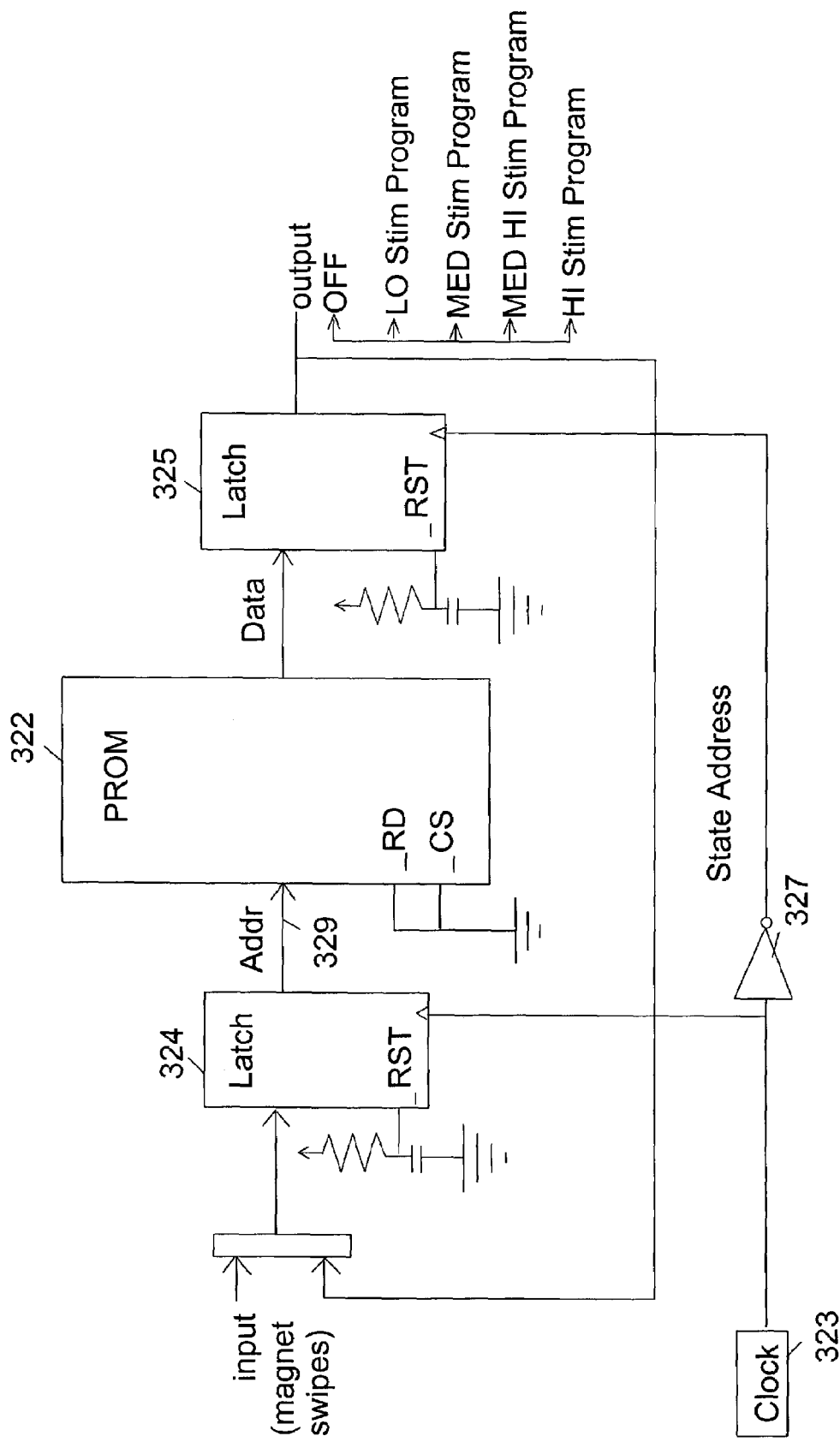
FIG. 36 is a schematic diagram depicting digital circuitry for state machine.

FIG. 36 shows a representative digital circuitry used for the basic state machine circuit. The circuit consists of a PROM 322 that has part of its data fed back as a state address. Other address lines 329 are used as circuit inputs, and the state machine changes its state address on the basis of these inputs. The clock 323 is used to pass the new address to the PROM 322 and then pass the output from the PROM 322 to the outputs and input state circuits. The two latches 324, 325 are operated 180° out of phase to prevent glitches from unexpectedly affecting any output circuits when the ROM changes state. Each state responds differently according to the inputs it receives.

Thus, in this embodiment the functioning of the system is similar to as described earlier. This embodiment though is cheaper to produce and offers limited programmability of the battery operated part of the system.

While the invention herein disclosed has been described by means of specific embodiments and applications thereof, numerous modifications and variation could be made thereto by those skilled in the art without departing from the scope of the invention set forth in the claims.

What is claimed is:

1. A method to provide electrical pulses to a vagus nerve(s) of a patient for providing therapy for at least one of neurological and neuropsychiatric disorders, comprising the steps of:
    providing an implanted stimulator, wherein said implanted stimulator comprises a microprocessor based programmable pulse generator module and a stimulus receiver module that receives external stimulus signals and is capable of applying said electrical pulses independently of said pulse generator module;
    providing an external programmer for programming said implanted stimulator;
    providing an external stimulator for inductively coupling to said stimulus receiver module;
    providing control circuitry that selectively operating one of said implanted pulse generator module and said stimulus receiver module; and
    providing an implanted lead in electrical contact with said implanted stimulator, and at least one electrode adapted to be in contact with said vagus nerve(s),
    whereby electric pulses are provided to said vagus nerve(s).

2. The method of claim 1, wherein said electrical pulses are provided anywhere along the length of said vagus nerve(s).

3. Method of claim 1, wherein said neurological and neuropsychiatric disorders further comprises partial complex epilepsy, generalized epilepsy, involuntary movement disorders caused by Parkinson's disease, migraines, neurogenic pain, depression, Alzheimer's disease, anxiety disorders, obsessive compulsive disorders, and the like.

4. The method of claim 1, wherein said vagus nerve(s) comprises at least one of left vagus nerve, right vagus nerve, or both vagus nerve(s).

5. Method of claim 1, wherein said external stimulator comprising telemetry means for remotely controlling said external stimulator.

6. Method of claim 1, wherein said external stimulator comprises means for networking with remote computers.

7. Method of claim 1, wherein said external stimulator further comprises a global positioning system (GPS) module for determining patient location.

8. Method of claim 1, wherein said external stimulator can be utilized to determine dose of electrical stimulation provided to said vagus nerve(s).

9. Method of claim 1, wherein said implanted pulse stimulator generator further comprises rechargeable power source, and is capable of being recharged via an external power source.

10. A method to provide therapy for central nervous system disorders using pulsed electrical stimulation to a vagus nerve(s) of a patient, comprising the steps of:
    providing an implanted stimulator; wherein said implanted stimulator comprises a pulse generator module and a stimulus receiver module that receives external stimulus signals and is capable of applying said pulsed electrical stimulation independently of said pulse generator module;
    providing an external stimulator with adjustable programs of stimulation, for inductively coupling to said implanted stimulus receiver;
    providing a lead in electrical contact with said implantable stimulator, and at least one electrode adapted to be in contact with said vagus nerve;
    determining suitable stimulation program for said patient, using said external stimulator; and
    programming said implanted stimulator with said suitable stimulation program using an external programming means,
    whereby said pulsed electrical stimulation is delivered to said vagus nerve(s).

11. Method of claim 10, wherein said implanted pulse generator module further comprises rechargeable power source.

12. Method of claim 10, wherein said implanted stimulator further comprises a circuitry means for selectively operating one of said stimulus receiver module and said pulse generator module.

13. Method of claim 10, wherein said external stimulator comprising telemetry means for remotely controlling said external stimulator.

14. Method of claim 10, wherein said external stimulator is networked with remote computers.

15. Method of claim 10, wherein said external programming means comprises a global positioning system (GPS) means for determining patient location.

16. A system comprising implantable and external components for providing pulsed electrical stimulation to a vagus nerve(s) of a patient, to provide therapy for one of neurological, neuropsychiatric disorders, comprising:
    an implantable stimulator, wherein said implantable stimulator comprising a pulse generator module and a stimulus receiver module that receives external stimulus signals and is capable of applying said pulsed electrical stimulation independently of said pulse generator module;

an external stimulator for inductively coupling to said stimulus receiver;

an external programmer for programming said implanted stimulator;

control circuitry incorporated within said implanted stimulator; and an implanted lead comprising at least one electrode adapted to be in contact with said vagus nerve(s);

whereby said pulsed electrical stimulation is provided to said vagus nerve(s).

17. The method of claim 16, wherein said electrical pulses are provided anywhere along the length of said vagus nerve(s).

18. The method of claim 16, wherein said vagus nerve(s) comprises at least one of left vagus nerve, right vagus nerve, or both vagus nerve(s).

19. System of claim 16, wherein said neurological and neuropsychiatric disorders further comprises partial complex epilepsy, generalized epilepsy, involuntary movement disorders caused by Parkinson's disease, or like, migraines, neurogenic pain, depression, Alzheimer's disease, anxiety disorders, obsessive compulsive disorders, and the like.

20. System of claim 16, wherein said external stimulator comprises telemetry module for remotely controlling said external stimulator.

21. System of claim 20, wherein said remote control is over the internet.

22. System of claim 16, wherein said external stimulator is networked with remote computers.

23. System of claim 16, wherein said external stimulator comprises a global positioning system (GPS) module for patient location.

24. A system for neuromodulation of a vagus nerve(s) of a patient for providing therapy for one of neurological and neuropsychiatric disorders, comprising:

an implantable stimulator, wherein said implantable stimulator comprising a stimulus receiver module, and a pulse generator module programmable with a magnet;

an external stimulator for inductively coupling to said stimulus receiver;

circuitry means to selectively operate one of said pulse generator module and said stimulus receiver module; and an implantable lead with at least one electrode adopted to be in contact with said vagus nerve(s), whereby said pulsed electrical stimulation is provided to said vagus nerve(s) selectively by either external stimulator/stimulus receiver module or implanted pulse generator module.

25. System of claim 24, wherein said external stimulator comprises a global positioning system (GPS) module for determining patient location.

26. System of claim 24, wherein said neurological and neuropsychiatric disorders further comprises from a group consisting of partial complex epilepsy, generalized epilepsy, involuntary movement disorders caused by Parkinson's disease, migraines, neurogenic pain, depression, Alzheimer's disease, anxiety disorders, obsessive compulsive disorders, and the like.

27. System of claim 24, wherein said external stimulator comprises telemetry module for remotely controlling said external stimulator.

28. System of claim 24, wherein said external stimulator is networked with remote computers.

29. A system for providing electrical stimulation to a vagus nerve(s) for providing therapy for one of partial complex epilepsy, generalized epilepsy, involuntary movement disorders caused by Parkinson's disease, migraines, depression, Alzheimer's disease, anxiety disorders, obsessive compulsive disorders, and the like, comprising:

an implantable stimulator comprising a pulse generation module and a stimulus receiver module, that receives external signals and is capable of applying said electrical stimulation independently of said pulse generation module wherein said implantable stimulator is adapted to be rechargeable with an external power source;

an external power source to recharge said implantable stimulator; and an implantable lead adapted to connected to said implantable stimulator with at least one electrode adapted to be in contact with said vagus nerve(s), whereby said therapy is provided using said rechargeable system.

30. The method of claim 29, wherein said vagus nerve(s) comprises at least one of left vagus nerve, right vagus nerve, or both vagus nerve(s).

* * * * *